US008715189B2

(12) United States Patent
Kanayama et al.

(10) Patent No.: US 8,715,189 B2
(45) Date of Patent: May 6, 2014

(54) ULTRASONIC DIAGNOSIS APPARATUS FOR SETTING A 3D ROI USING VOXEL VALUES AND OPACITY

(75) Inventors: Yuko Kanayama, Otawara (JP); Naohisa Kamiyama, Otawara (JP); Yoko Okamura, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 747 days.

(21) Appl. No.: 12/976,382

(22) Filed: Dec. 22, 2010

(65) Prior Publication Data

US 2011/0172531 A1 Jul. 14, 2011

(30) Foreign Application Priority Data

Jan. 8, 2010 (JP) ................................. 2010-003301

(51) Int. Cl.
*A61B 5/05* (2006.01)

(52) U.S. Cl.
USPC ........................... 600/443; 382/128; 345/419

(58) Field of Classification Search
USPC .......... 600/437, 443; 382/128, 276, 285, 302; 345/419–421, 424, 584, 585, 606, 619, 345/653, 656, 441
See application file for complete search history.

(56) References Cited

U.S. PATENT DOCUMENTS

| | | | | |
|---|---|---|---|---|
| 5,319,551 A | * | 6/1994 | Sekiguchi et al. | 382/131 |
| 5,514,957 A | * | 5/1996 | Tatebayashi | 324/309 |
| 5,671,157 A | * | 9/1997 | Saito | 345/419 |
| 2005/0143639 A1 | * | 6/2005 | Matsumoto | 600/407 |

FOREIGN PATENT DOCUMENTS

| | | | |
|---|---|---|---|
| JP | 2004187743 | * | 7/2004 |
| JP | 2005322257 | * | 11/2005 |
| JP | 2006000127 | * | 1/2006 |

OTHER PUBLICATIONS

Office Action mailed Nov. 5, 2013, in Japanese Patent Application No. 2010-003301, filed Jan. 8, 2010 (with English-Language Translation), 7 pages.

* cited by examiner

*Primary Examiner* — Parikha Mehta
(74) *Attorney, Agent, or Firm* — Oblon, Spivak, McClelland, Maier & Neustadt, L.L.P.

(57) ABSTRACT

According to one embodiment, an ultrasonic diagnosis apparatus includes an ultrasonic probe, an ultrasonic transmission/reception unit, a volume data generating unit, a projected image generating unit, a two dimensional region-of-interest setting unit, a specifying unit, a calculation unit and a three-dimensional region-of-interest determination unit. The specifying unit specifies cells on rays which pass through the respective pixels in the 2D-ROI and are used to acquire a VR image. The calculation unit calculates the contribution degree of each cell based on the voxel value and opacity of each cell specified and calculates the average value of the contribution degrees of cells equal in distance from the screen of the VR image along the line-of-sight direction. The three-dimensional region-of-interest determination unit specifies the distances from the screen of the VR image which correspond to average contribution values exceeding the predetermined threshold and determines the position of the 3D-ROI in the volume data.

16 Claims, 16 Drawing Sheets

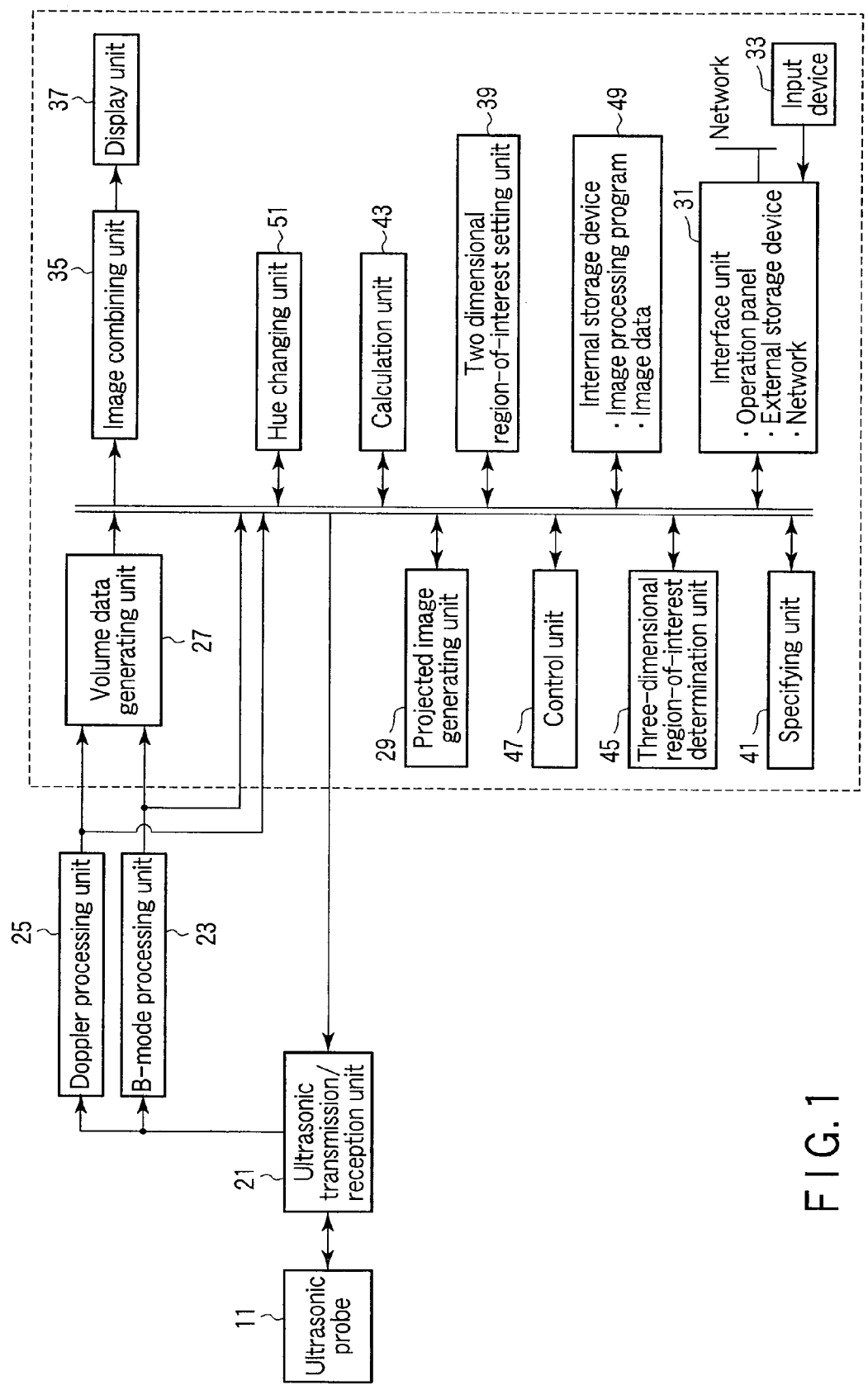
F I G. 1

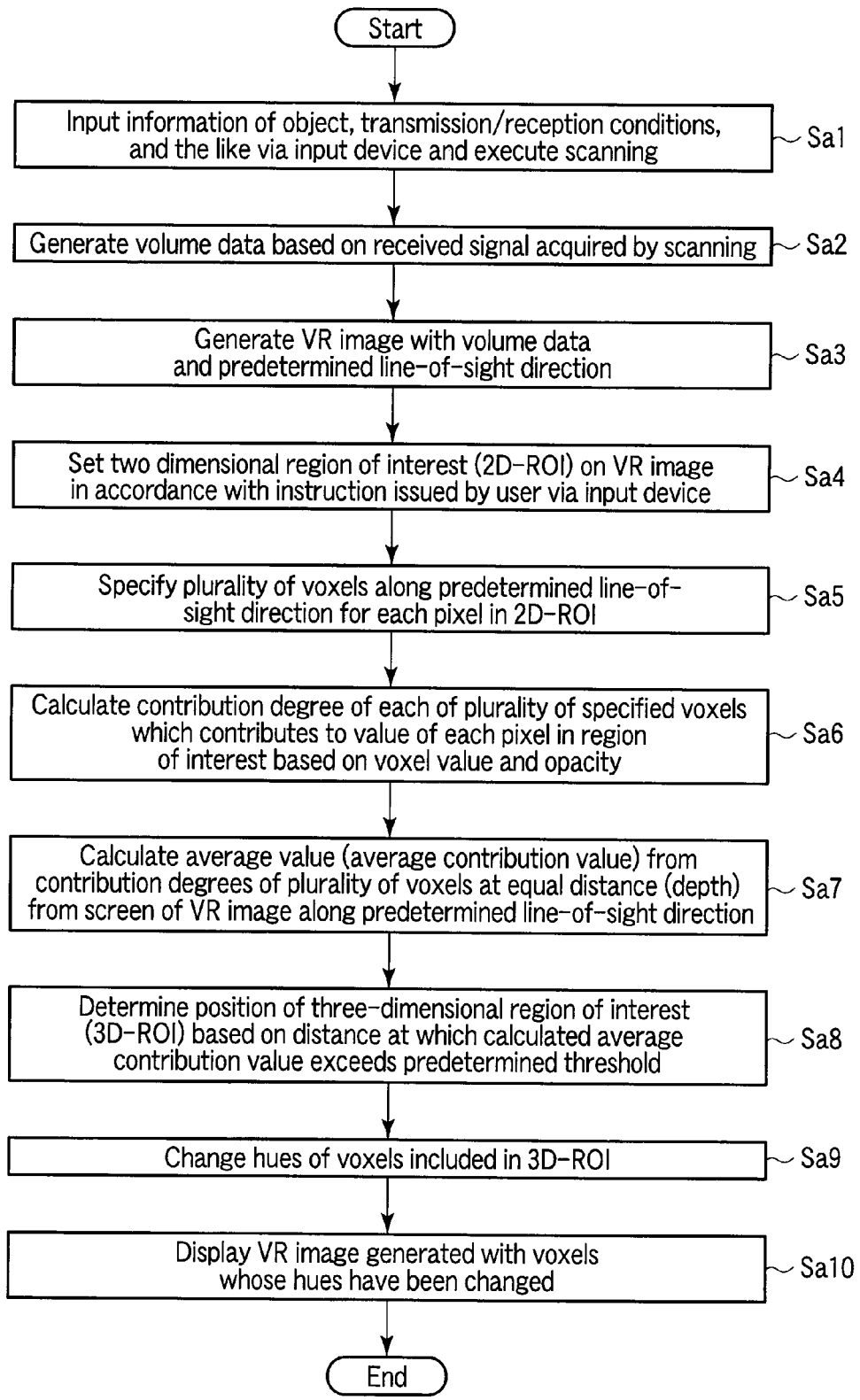
F I G. 4

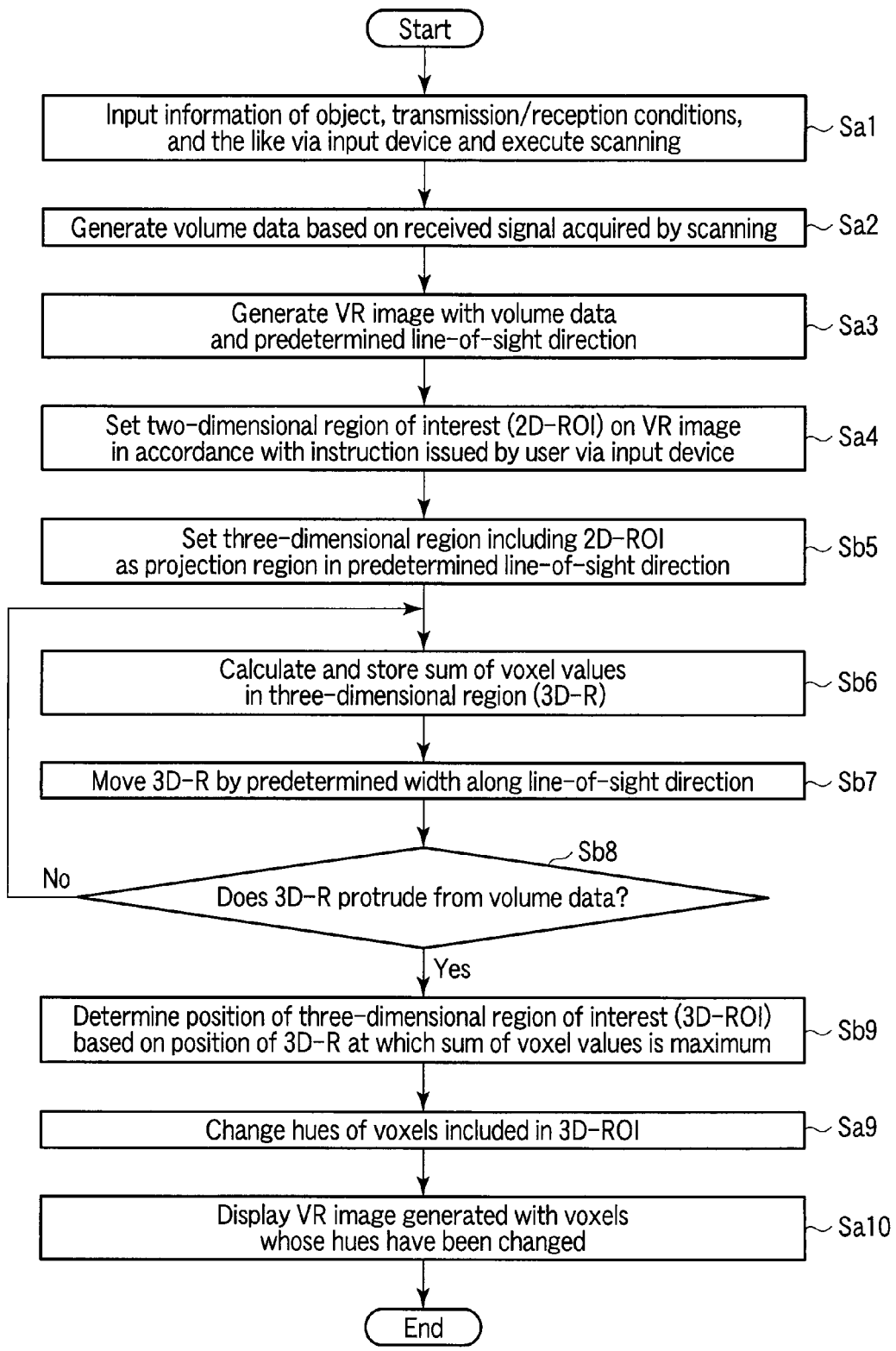
F I G. 8

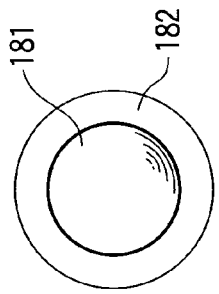
F I G. 12
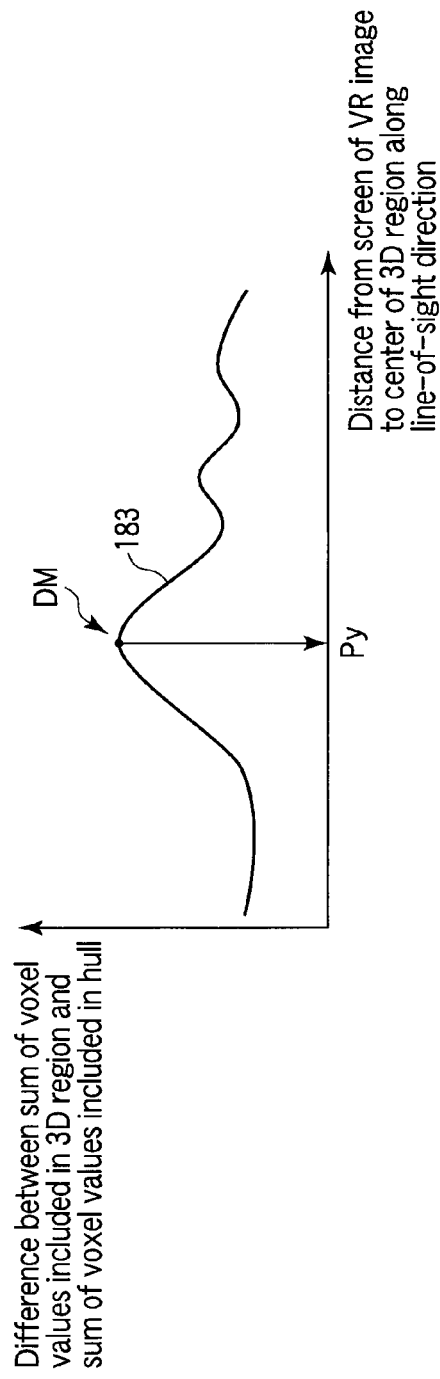
F I G. 13

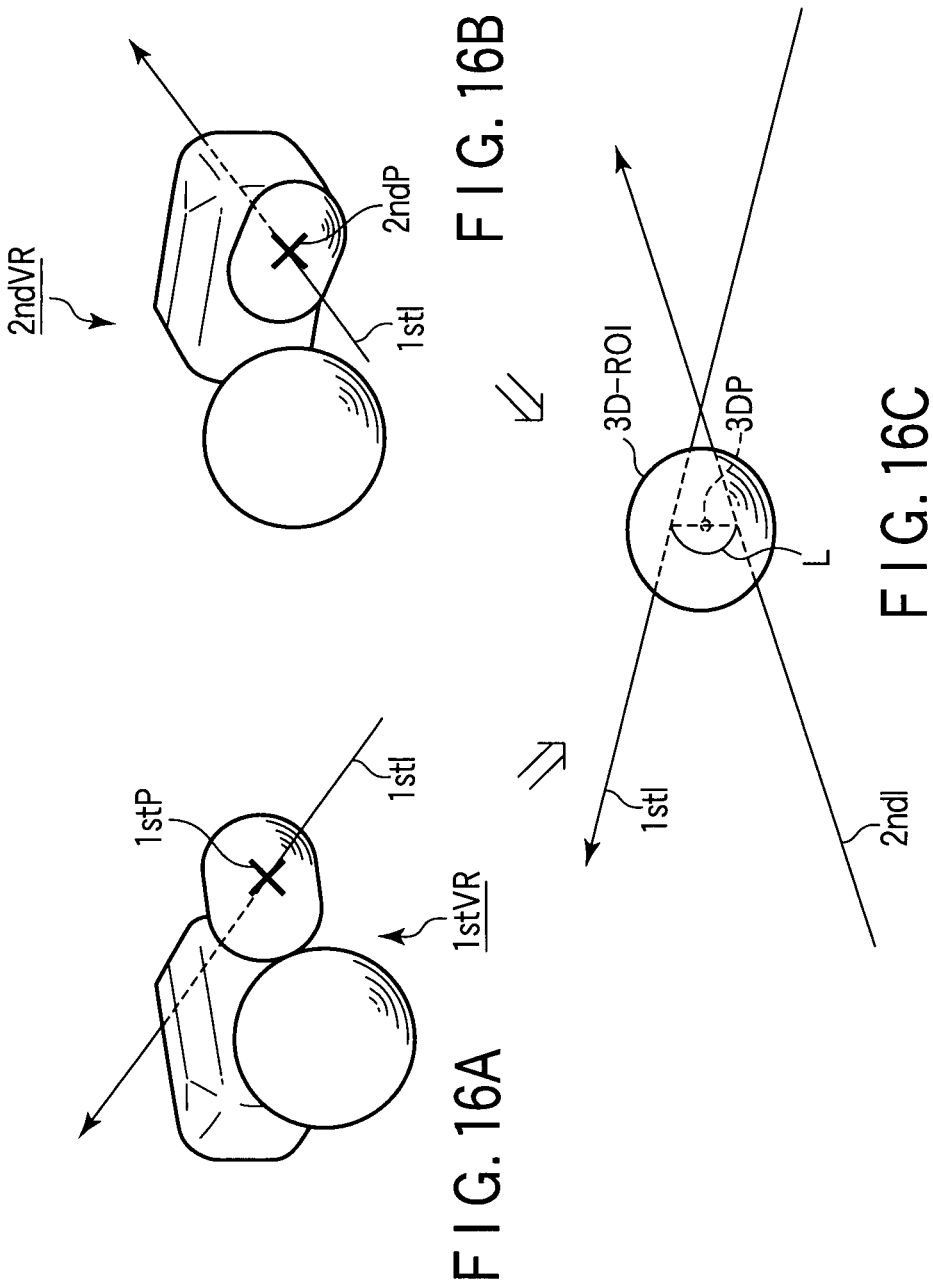
F I G. 16A
F I G. 16B
F I G. 16C

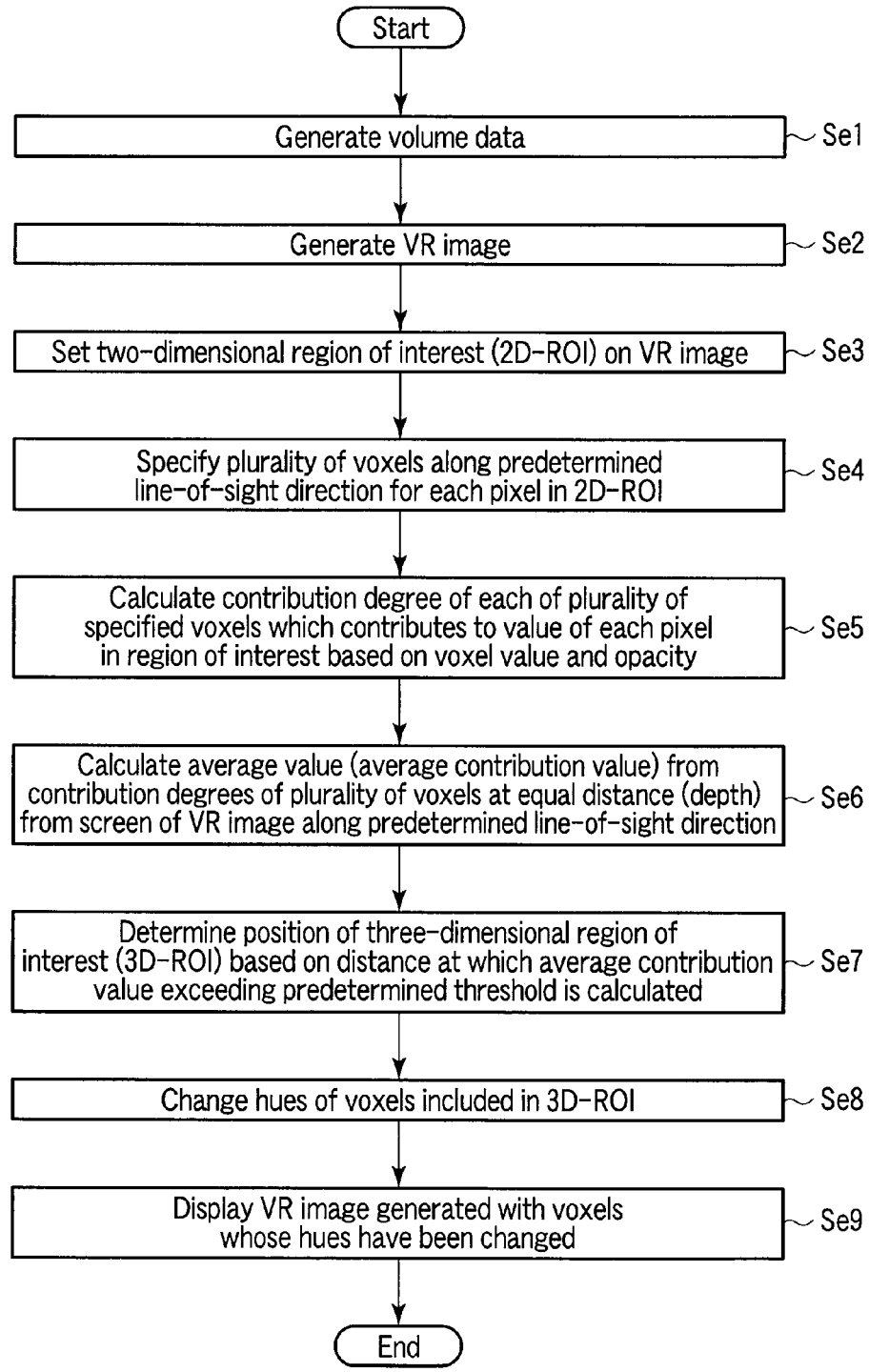
F I G. 17

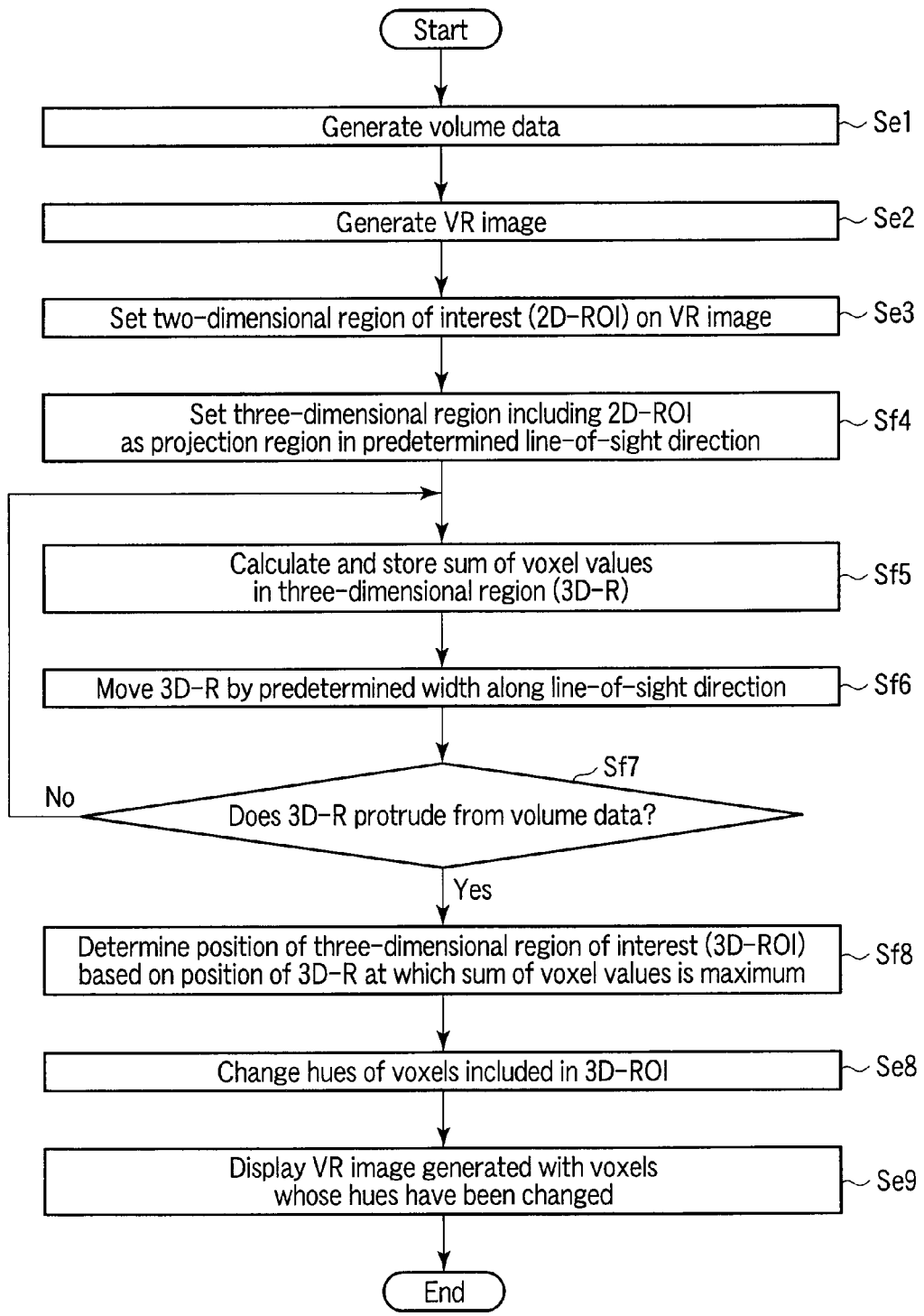
F I G. 18

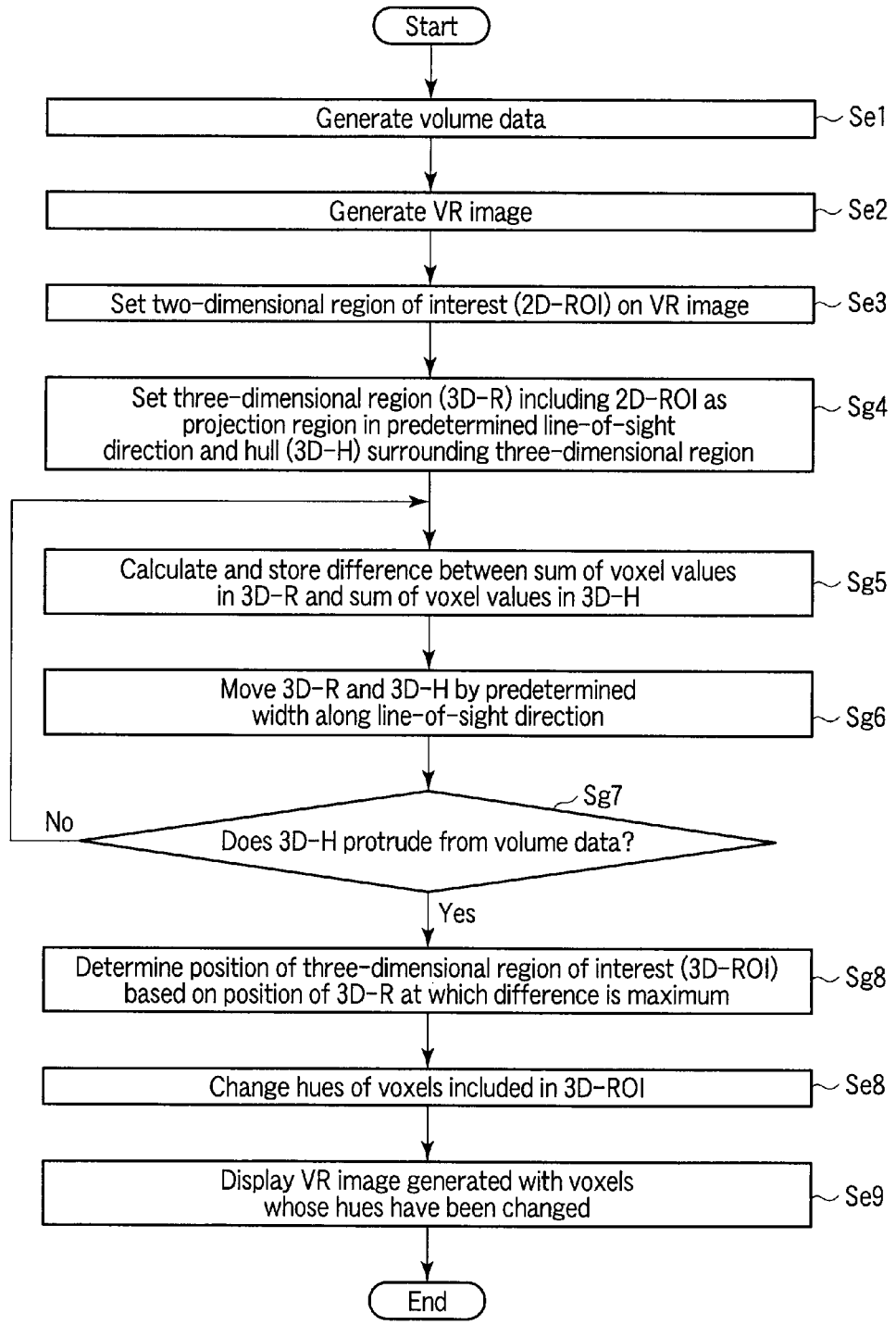
F I G. 19

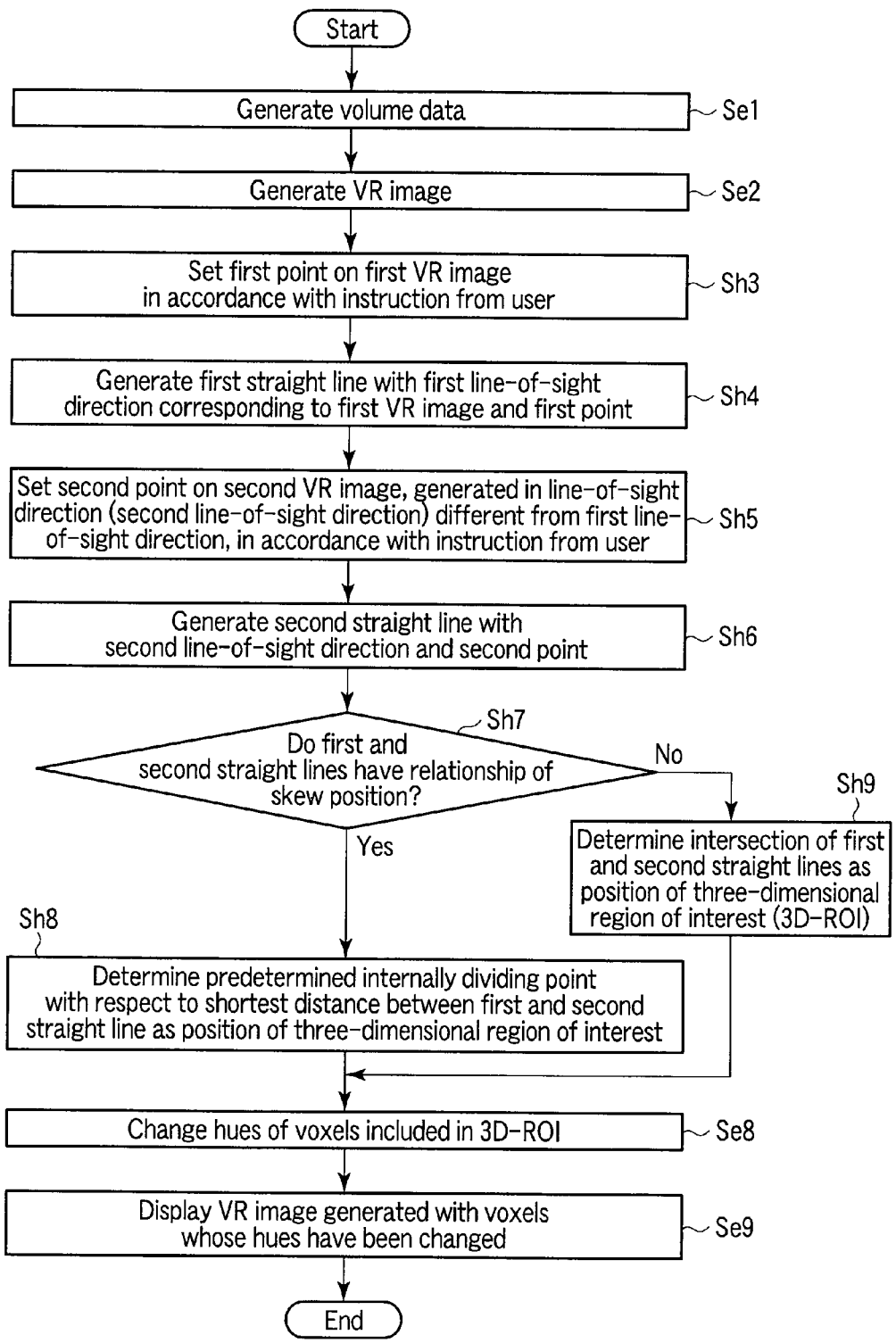
F I G. 20

ULTRASONIC DIAGNOSIS APPARATUS FOR SETTING A 3D ROI USING VOXEL VALUES AND OPACITY

CROSS-REFERENCE TO RELATED APPLICATIONS

This application is based upon and claims the benefit of priority from Japanese Patent Application No. 2010-003301, filed Jan. 8, 2010; the entire contents of which are incorporated herein by reference.

FIELD

Embodiments described herein relate generally to an ultrasonic diagnosis apparatus, medical image processing apparatus, and medical image diagnosis apparatus.

BACKGROUND

Various types of current image diagnosis apparatuses can obtain three-dimensional image data (to be referred to as volume data hereinafter) as well as a two-dimensional image of one slice. There have been proposed various display methods which allow users to easily analyze obtained volume data.

Methods of displaying volume data which are generally and frequently used include, for example, a method of displaying three arbitrary slices (to be referred to as MPR (MultiPlanar Reconstruction) images hereinafter) perpendicular to each other and a method of displaying a projected image from a given line-of-sight direction by volume rendering (to be referred to as VR hereinafter). The user can freely observe a region that he/she wants to view, from a desired direction, by changing the positions of these arbitrary slices or changing the line-of-sight direction on a volume rendering image (to be referred to as a VR image hereinafter).

When observing a VR image in this manner, the user sometimes loses sight of a point or region on which he/she has focused his/her attention (to be referred to as a target region hereinafter) while rotating the displayed image or changing a region displayed on a VR image. With regard to this point, marking a target region on a VR image will facilitate analysis on volume data. A VR image is a two-dimensional image, where a target object with depth information is projected on one screen. For this reason, unlike setting an ROI (Region Of Interest to be referred to as a 2D-ROI hereinafter) in a two-dimensional slice (two-dimensional image), simply setting a 2D-ROI on a VR image will not determine its position in volume data. That is, it is not possible to uniquely designate a target region.

When setting a three-dimensional region of interest (to be referred to as a 3D-ROI hereinafter) in volume data, the user conventionally uses a method of designating a corresponding region in an arbitrary slice. When, for example, designating a measurement region at the time of volume measurement, the apparatus displays an arbitrary slice image including a target stereoscopic region. The user then designates several points on the displayed slice image to create a closed curve. The user rotates the volume data relative to a predetermined axis in a slice including the created closed curve. The user designates points on another slice based on the rotated volume data by a method similar to the above operation. Repeating such a series of operations can specify the region designated by the user in the end. In addition, since closed curves are created on a plurality of MPR images, it is possible to create a 3D-ROI with a relatively complex shape. In addition, in order to reduce the load on the user, it is possible to designate one point on an arbitrary slice and create a 3D-ROI in a spherical shape including a predetermined radius, instead of a complex shape, in volume data.

Setting a 3D-ROI in the volume data allows the user to freely observe a desired region from a desired direction without losing sight of it.

BRIEF DESCRIPTION OF THE DRAWING

FIG. 1 is a block diagram showing the arrangement of an ultrasonic diagnosis apparatus according to the first embodiment;

FIG. 4 is a flowchart showing a procedure for determining a 3D-ROI based on a 2D-ROI set on a VR image in the first embodiment;

FIG. 8 is a flowchart showing a procedure for determining a 3D-ROI based on a three-dimensional region including a 2D-ROI as a projection of a predetermined line-of-sight direction in the second embodiment;

FIG. 12 is a view showing an example of a three-dimensional region and an example of the hull surrounding the three-dimensional region;

FIG. 13 is a graph of the differences between the sums of the voxel values included in a three-dimensional region which correspond to the distances from the screen of a VR image to the center of the three-dimensional region along the line-of-sight direction and the sums of the voxel values included in the hull surrounding the three-dimensional region;

FIGS. 16A, 16B, and 16C are views each showing an example of the position of a 3D-ROI in volume data which is determined by the shortest distance between the first and second straight lines according to the fourth embodiment;

FIG. 17 is a flowchart showing a procedure for determining a 3D-ROI based on a 2D-ROI set on a VR image in the fifth embodiment;

FIG. 18 is a flowchart showing a procedure for determining a 3D-ROI based on a three-dimensional region including a 2D-ROI as its projection with in a predetermined line-of-sight direction in the sixth embodiment;

FIG. 19 is a flowchart showing a procedure for determining a 3D-ROI based on a three-dimensional region including a 2D-ROI as its projection with a predetermined line-of-sight direction in the seventh embodiment; and FIG. 20 is a flowchart showing a procedure for determining a 3D-ROI based on two line-of-sight directions which are not parallel in the eighth embodiment.

DETAILED DESCRIPTION

Figure 2:
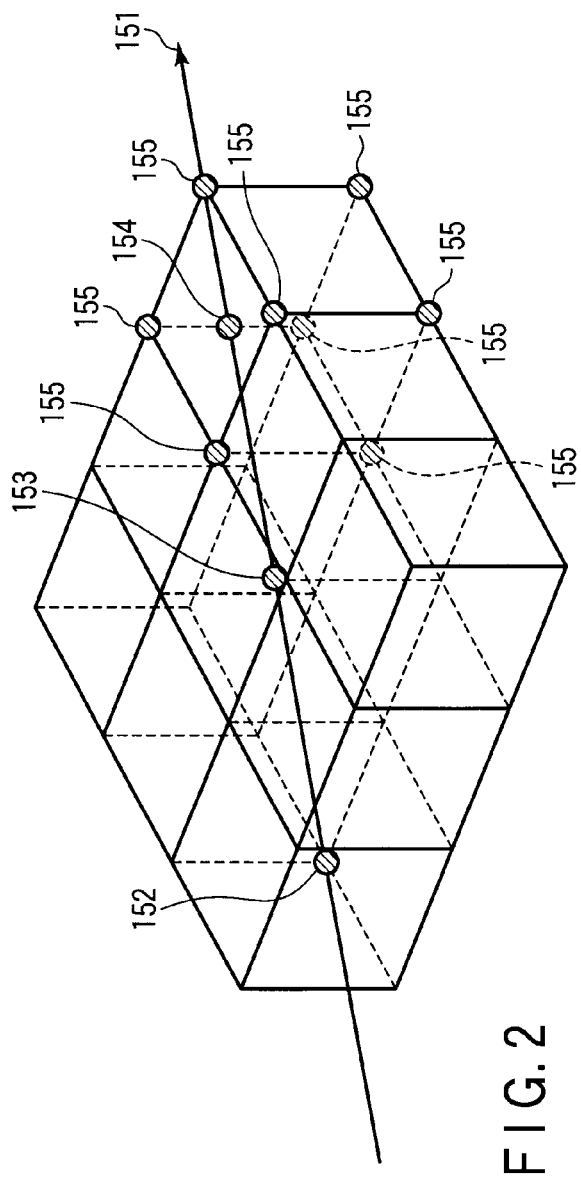
FIG. 2 is a view showing an example for explaining a ray casting method to be used to generate a VR image according to the first embodiment.

In general, according to one embodiment, an ultrasonic diagnosis apparatus includes an ultrasonic probe, an ultrasonic transmission/reception unit, a volume data generating unit, a projected image generating unit, a two-dimensional region-of-interest setting unit, a specifying unit, a calculation unit, and a three-dimensional region-of-interest determination unit. The ultrasonic transmission/reception unit transmits an ultrasonic wave to an object and receives a reflected wave corresponding to the transmitted ultrasonic wave from the object via the ultrasonic probe, and generates a received signal based on the received reflected wave. The volume data generating unit generates volume data based associated with a predetermined region of the object on the received signal. The projected image generating unit generates a projected image using the volume data and a predetermined line-of-sight direction. The two-dimensional region-of-interest region setting unit sets a two-dimensional region of interest on the projected image in accordance with an instruction from a user. The specifying unit specifies a plurality of voxels in volume data along the predetermined line-of-sight direction for each pixel in the two-dimensional region of interest. The calculation unit calculates the contribution degree of each of a plurality of voxels which contributes to the value of each pixel in a two-dimensional region of interest based on the voxel value and opacity of each voxel. The three-dimensional region-of-interest determination unit determines the position of a three-dimensional region of interest in the volume data which corresponds to the two-dimensional region of interest based on the contribution degrees.

An embodiment will be described below with reference to the views of the accompanying drawing. Note that the same reference numerals denote constituent elements including almost the same functions and arrangements, and a repetitive description will be made only when required.

(First Embodiment)

The first embodiment will be described below with reference to the views of the accompanying drawing.

FIG. 1 is a block diagram showing the arrangement of an ultrasonic diagnosis apparatus according to this embodiment. Referring to FIG. 1, this ultrasonic diagnosis apparatus includes an ultrasonic probe 11, an ultrasonic transmission/reception unit 21, a B-mode processing unit 23, a Doppler processing unit 25, a volume data generating unit 27, a projected image generating unit 29, an interface unit 31, an input device 33, an image combining unit 35, a display unit 37, a two-dimensional region-of-interest setting unit 39, a specifying unit 41, a calculation unit 43, a three-dimensional region-of-interest determination unit 45, a control unit 47, an internal storage device 49, and a hue changing unit 51. In addition, a network and biometric signal measuring units (not shown) typified by an electrocardiograph, phonocardiograph, sphygmograph, and respiration sensor may be connected to the ultrasonic diagnosis apparatus via the interface unit 31. Note that when the technical idea of this ultrasonic diagnosis apparatus is to be implemented by a medical image processing apparatus, the apparatus has, for example, the arrangement enclosed by the dotted line in FIG. 1.

The ultrasonic probe 11 includes piezoelectric vibrators as acoustoelectric reversible conversion elements such as piezoelectric ceramics. A plurality of piezoelectric vibrators are juxtaposed and mounted on the distal end of the ultrasonic probe 11. Note that the following description is based on the assumption that one vibrator forms one channel.

The ultrasonic transmission/reception unit 21 includes a rate pulse generator, transmission delay circuit, pulser, amplification circuit, A/D converter, beam former, and adder (not shown). The rate pulse generator repeatedly generates rate pulses for the formation of transmission ultrasonic waves at a predetermined rate frequency. The transmission delay circuit gives each rate pulse a delay time necessary to focus an ultrasonic wave into a beam and determine transmission directivity for each channel. The pulser applies a driving pulse to each vibrator at the timing based on this rate pulse to form an ultrasonic beam toward a predetermined scanning line. The amplification circuit amplifies an echo signal from the object received via the ultrasonic probe 11 for each channel. The A/D converter converts an amplified echo signal, which is an analog signal, into digital signal for each channel. The beam former gives the digital echo signals delay times necessary to determine reception directivities. The adder then adds a plurality of echo signals in accordance with a reception delay pattern from the control unit 47. This addition enhances a reflection component from a direction corresponding to the reception directivity. The transmission directivity and the reception directivity determine the synthetic directivity of ultrasonic transmission/reception (which determines so-called "ultrasonic scanning lines").

The B-mode processing unit 23 receives an echo signal from the ultrasonic transmission/reception unit 21, and performs logarithmic amplification, envelope detection processing, and the like for the signal to generate B-mode data whose signal intensity is expressed by a brightness level. The volume data generating unit 27 performs predetermined processing for the generated B-mode data.

The Doppler processing unit 25 performs Doppler processing based on an echo signal from the ultrasonic transmission/reception unit 21. The Doppler processing is the processing of frequency-analyzing velocity information to extract a blood flow, tissue, and contrast medium echo component by the Doppler effect, and obtaining blood flow information such as an average velocity, variance, and power. The volume data generating unit 27 performs predetermined processing for the data including undergone Doppler processing (to be referred to as Doppler data hereinafter).

The volume data generating unit 27 arranges (arrangement processing) B-mode data from the B-mode processing unit 23 or Doppler data from the Doppler processing unit in a dedicated memory in accordance with position information. The volume data generating unit 27 then interpolates (interpolation processing) B-mode data or Doppler mode between ultrasonic scanning lines. The volume data generating unit 27 converts the scanning line signal for ultrasonic scanning generated by the arrangement processing and interpolation processing into a scanning line signal in a general video format typified by a TV format. The volume data generating unit 27 generates volume data constituted by a plurality of voxels. Each voxel has a voxel value corresponding to the intensity of the corresponding B-mode data or Doppler data. Note that data before it is input to the volume data generating unit 27 will be referred to as "raw data".

The projected image generating unit 29 generates two-dimensional display image data by performing three-dimensional image processing for volume data. Three-dimensional image processing includes VR using the ray casting method and surface rendering. Alternatively, this processing may be MIP (Maximum Intensity Projection) or MPR processing. Assume that the projected image generating unit 29 generates a VR image by performing VR using the ray casting method as three-dimensional image processing.

VR will be described below with reference to FIG. 2. The volume data generated by the volume data generating unit 27 is constituted by a plurality of voxel data. Each voxel constituting a volume has a value of brightness as voxel value (voxel data). The projected image generating unit 29 determines the opacity of each voxel with its voxel value. Assume that a voxel in FIG. 2 exists at a vertex (for example, 155) of each cube. When the user sets a line-of-sight direction via the input device 33, the apparatus simultaneously sets a projection plane (screen) perpendicular to the line-of-sight direction. Subsequently, the projected image generating unit 29 determines a plurality of rays which pass through pixels in the projection plane and are parallel to the line-of-sight direction. FIG. 2 shows an example in which a given ray 151 passes through part of the volume. FIG. 2 also shows an example of a cell 154 including a voxel value x and opacity a calculated by linear interpolation based on the voxel values and opacities of eight adjacent voxels 155. Each cell exists on a ray like a cell 152 or 153 in FIG. 2. Note that a predetermined line-of-sight direction may be one line-of-sight direction as in the case of parallel projection shown in FIG. 2, or a plurality of line-of-sight directions may be set as in the case of perspective projection.

The projected image generating unit 29 accumulates voxel values based on a voxel value xk and opacity αk of a cell Pk on a ray Lk which is projected as a point on the kth pixel in a projection plane. More specifically, an accumulated voxel value Ikout(i) passing through an ith cell Pk(i) along a ray from the projection plane can be calculated by $$Ikout(i)=Ikin(i)\times(1-\alpha k(i))+xk(i)\times\alpha k(i)$$

where Ikin(i) is the accumulated voxel value applied from the projection plane to the ith cell Pk(i) along the ray Lk, αk(i) is the opacity of the cell Pk(i), and xk(i) is the voxel value of the cell Pk(i). Note that the accumulated voxel value Ikout(i) is an accumulated voxel value Ikin(i+1) applied to a cell Pk(i+1).

The projected image generating unit 29 accumulates opacities of a plurality of cells on a given ray while accumulating voxel values. When a ray reaches outside the volume data or the accumulated opacity reaches 1, the projected image generating unit 29 terminates this accumulation for this ray. At this time, the accumulated voxel value is set as the value of a pixel on the projection plane which is associated with this ray. In the same manner, the projected image generating unit 29 accumulates voxel values and opacities of a plurality of cells on other rays. Upon acquiring the accumulated voxel values of all the pixels in the projection plane, the projected image generating unit 29 outputs the pixel values (accumulated voxel values) in the projection plane to the image combining unit 35.

The interface unit 31 is an interface for the input device 33, a network, and external storage devices and biometric signal measuring units (none of which are shown). The interface unit 31 can transfer data such as ultrasonic images, analysis results, and the like obtained by this ultrasonic diagnosis apparatus to other apparatuses through the network.

The input device 33 is connected to the interface unit 31 to input various kinds of commands, instruction, information, selections, and settings from the user to this ultrasonic diagnosis apparatus. Although not shown, the input device 33 includes input devices such as a trackball, switch buttons, mouse, and keyboard which are used to set a 2D-ROI and the like. An input device detects the coordinates of the cursor displayed on the display screen and outputs the detected coordinates to the control unit 47. Note that the input device may be a touch panel covering the display screen. In this case, the input device 33 detects touched/designated coordinates by, for example, an electromagnetic induction, electro-magnetostriction, or pressure sensitive scheme, and outputs the detected coordinates to the control unit 47. The input device 33 inputs at least the slice position or slice direction of the display image generated by the projected image generating unit 29 or at least the line-of-sight position or line-of-sight direction on the display image in accordance with the operation of the input device by the user. The input device 33 also sets/designates a 2D-ROI in accordance with the operation of the input device by the user. When, for example, the operator operates the end button or FREEZE button of the input device 33, the transmission/reception of ultrasonic waves is terminated, and the ultrasonic diagnosis apparatus is set in a temporary stop state.

The image combining unit 35 combines an ultrasonic image as a projected image received from the projected image generating unit 29 with various kinds of parameters, a biometric signal (e.g., an electrocardiographic waveform, phonocardiographic waveform, sphygmographic waveform, or respiration curve) received from a biometric signal measuring unit (not shown), a 2D-ROI set by the two-dimensional region-of-interest setting unit 39 (to be described later), scale marks, and the like, and outputs the combined image as a video signal to the display unit 37.

Figure 3B:
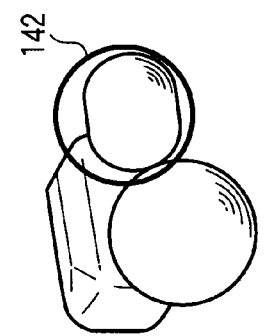
FIGS. 3A and 3B are views respectively showing an example of a VR image and an example of a 2D-ROI set on the VR image by an interpreting doctor or the like according to the first embodiment.
Figure 3A:
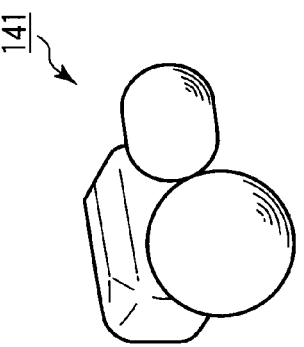

The display unit 37 displays an ultrasonic image as a projected image based on a video signal from the image combining unit 35. FIG. 3A shows an example of a VR image displayed on the display unit 37.

The two-dimensional region-of-interest setting unit 39 sets a 2D-ROI on the image displayed on the display unit 37 in accordance with the instruction input by the user via the input device 33.

The specifying unit 41 specifies cells on rays which pass through the respective pixels in the 2D-ROI set by the two-dimensional region-of-interest setting unit 39 and are used to acquire a VR image. For example, the specifying unit 41 specifies a plurality of rays which pass through the respective pixels in the 2D-ROI set by the two-dimensional region-of-interest setting unit 39 and are parallel to the line-of-sight direction set by the user via the input device 33. Subsequently, the specifying unit 41 specifies a plurality of cells on the plurality of specified rays.

The calculation unit 43 calculates the contribution degree of each cell which contributes to the value of each pixel in a 2D-ROI based on the voxel value and opacity of each cell specified by the specifying unit 41. The calculation unit 43 calculates the average value of the contribution degrees of a plurality of cells equal in distance from the screen of the VR image along the line-of-sight direction. This average value will be referred to as an average contribution value. The internal storage device 49 stores average contribution values in correspondence with the information of distances from the screen of a VR image along the line-of-sight direction.

The three-dimensional region-of-interest determination unit 45 determines whether the average contribution value calculated by the calculation unit 43 exceeds a predetermined threshold, in the ascending order of the distances from the screen of the VR image. Subsequently, the three-dimensional region-of-interest determination unit 45 specifies the distances from the screen of the VR image which correspond to average contribution values exceeding the predetermined threshold for the first time. The three-dimensional region-of-interest determination unit 45 determines the position of the 3D-ROI in the volume data based on the specified distances from the screen of the VR image. The predetermined threshold is, for example, an average contribution value set for each lesion. Note that it is possible to store in advance, in the internal storage device 49, predetermined thresholds for diagnostic targets, diseases, lesions, and the like as a template, and change the thresholds in accordance with the instruction issued by the user via the input device 33, as needed. The interpreting doctor or the like can change the size of a determined 3D-ROI via the input device 33, as needed, while observing a displayed projected image.

The control unit 47 reads out transmission/reception conditions and an apparatus control program stored in the internal storage device 49 based on the mode selection information, ROI setting, reception delay pattern list selection information, and transmission start/end information input by the user via the input device 33, and controls this ultrasonic diagnosis apparatus in accordance with these pieces of information. The control unit 47 reads out a dedicated program (a three-dimensional region-of-interest determination function to be described later) for determining the position of a 3D-ROI in volume data which corresponds to the 2D-ROI set by the two-dimensional region-of-interest setting unit 39 and a control program for implementing a predetermined image generation/display operation or the like from the internal storage device 49, expands the programs in the memory, and executes computation/processing and the like associated with each kind of processing.

The internal storage device 49 stores a plurality of reception delay patterns with different focal depths, a control program for the apparatus, a diagnostic protocol, various kinds of data groups such as transmission/reception conditions, the B-mode data and Doppler data generated by the B-mode processing unit 23 and the Doppler processing unit 25 for each scanning direction, the volume data generated by the volume data generating unit 27, the VR images generated by the projected image generating unit 29, the images combined by the image combining unit, the 2D-ROIs set by the two-dimensional region-of-interest setting unit 39, average contribution values associated with the distances from the screen of the VR images along the line-of-sight direction, predetermined thresholds used by the three-dimensional region-of-interest determination unit 45, a dedicated program for implementing the three-dimensional region-of-interest determination function, and the like.

The hue changing unit 51 changes the hues of a plurality of voxels included in the 3D-ROI determined by the three-dimensional region-of-interest determination unit 45.

The operation of a function (to be referred to as a 3D-ROI determination function hereinafter) for determining a 3D-ROI in volume data in this ultrasonic diagnosis apparatus will be described next with reference to the flowchart shown in FIG. 4.

Before ultrasonic transmission/reception for an object, the user inputs patient information and sets and updates transmission/reception conditions and various ultrasonic data acquisition conditions via the input device 33. The internal storage device 49 stores these settings and updated information. Upon completing these input/selecting/setting operations, the doctor brings the ultrasonic probe 11 into contact with the surface of the object at a predetermined position. The control unit 47 then transmits ultrasonic waves over a plurality of heartbeats in synchronism with an ECG waveform, and receives reflected waves corresponding to the transmitted ultrasonic waves (that is, performs ultrasonic scanning) (step Sa1). Note that in step Sa1, it is possible to transmit ultrasonic waves in synchronism with a phonocardiographic waveform, sphygmographic waveform, respiration curve, or the like.

The received signal based on the reception of received reflected waves is sent to the B-mode processing unit 23 or the Doppler processing unit 25. B-mode data or Doppler data is generated with the received signal. The generated B-mode data or Doppler data is sent to the volume data generating unit 27. The volume data generating unit 27 generates volume data with the B-mode data or Doppler data (step Sa2). A VR image is generated by VR using the generated volume data sent to the projected image generating unit 29 and the line-of-sight direction set in accordance with the instruction issued by the user via the input device 33 (step Sa3).

A 2D-ROI is set on the VR image displayed on the display unit 37 in accordance with the instruction issued by the user via the input device 33 (step Sa4). FIG. 3B is a view showing an example of setting a 2D-ROI 142 on the image shown in FIG. 3A which is the VR image displayed on the display unit 37.

Based on each ray used for VR in step Sa3, which passes through each pixel in the set 2D-ROI, a plurality of cells in the volume data which are located on the ray are specified (step Sa5). When, for example, the ray 151 shown in FIG. 2 passes through pixels in the 2D-ROI, the cells 152 and 153 in FIG. 2 are the cells to be specified (to be referred to as specified cells hereinafter).

The calculation unit 43 calculates a contribution degree contributing to the value of each pixel in the 2D-ROI based on the voxel value and opacity of each specific cell calculated when the projected image generating unit 29 generates a VR image (step Sa6). For example, the calculation unit 43 can calculate a contribution degree Jm(i) of an ith cell Pm(i) on a ray Lm passing through the mth pixel in the 2D-ROI according to the following equation:

$$Jm(i)=Imout(i)-Imin(i)=Imout(i)-Imout(i-1)$$

where Imout(i) is an accumulated voxel value passing through the ith cell Pm(i) on the ray Lm passing through the mth pixel in the 2D-ROI set on the VR image, and Imin(i) is an accumulated voxel value applied to the ith cell Pm(i) on the ray Lm. Note that the accumulated voxel value Imout(i−1) is the accumulated voxel value Imin(i) applied to the cell Pm(i).

The calculation unit 43 calculates an average contribution value from the contribution degrees of a plurality of cells equal in distance (depth) from the screen of the VR image to the volume data along a plurality of rays (step Sa7). It is possible to obtain an average contribution value by calculating the sum of a plurality of contribution degrees Jm(i) of an equal distance, and dividing the sum by the number of rays, i.e., the number of pixels in the 2D-ROI.

Figure 5:
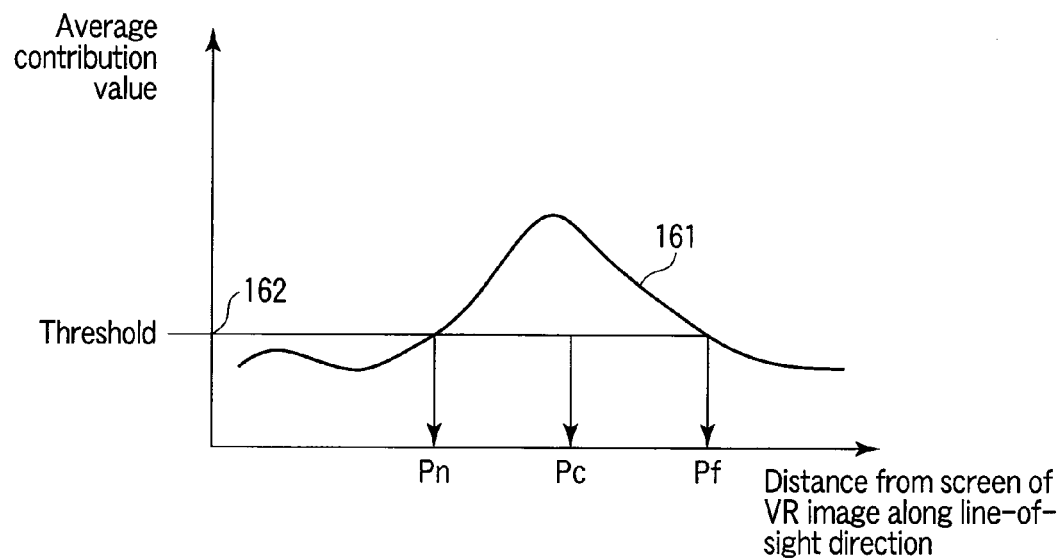
FIG. 5 is a graph of average contribution values corresponding to the distances from the screen of a VR image along the line-of-sight direction according to the first embodiment.

The position of a 3D-ROI in the volume data is determined based on the distance at which an average contribution value exceeds a predetermined threshold (step Sa8). FIG. 5 shows an example of average contribution values corresponding to distances from the screen of a VR image along the line-of-sight direction and the distances corresponding to average contribution values exceeding a predetermined threshold for the determination of a 3D-ROI. Referring to FIG. 5, reference numeral 161 denotes the curve obtained by plotting average contribution values corresponding to the distances from the screen of the VR image along the line-of-sight direction; and 162, a threshold for average contribution values for the determination of a 3D-ROI. Reference symbol Pn denotes the distance from the screen of the VR image at which the first average contribution value exceeds the predetermined threshold. The three-dimensional region-of-interest determination unit 45 determines the position of the 3D-ROI in the volume data based on the distance Pn. Assume that the position of the 3D-ROI determined based on the distance Pn is the frontmost surface of the 3D-ROI. Note that reference symbol Pf denotes an average contribution value exceeding a predetermined threshold at the farthest distance from the screen of the VR image along the line-of-sight direction on the 3D-ROI. In addition, reference symbol Pc denotes a midpoint between Pn and Pf. The three-dimensional region-of-interest determination unit 45 can determine the position of the rearmost surface or center of gravity of the 3D-ROI in the volume data based on Pf or Pc. If, for example, a 3D-ROI is spherical, it is possible to determine the position of the center of the 3D-ROI in the volume data based on Pc. Note that the user can set, via the input device 33, information indicating which part of the 3D-ROI is made to correspond to the position of the 3D-ROI determined based on Pn or Pf.

Figure 6A:
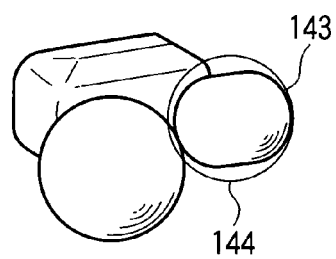
FIGS. 6A and 6B are views respectively showing an example of a VR image generated with voxels whose hues are changed in a 3D-ROI and the 3D-ROI and an example of a VR image on which the line-of-sight direction is changed according to the first embodiment.
Figure 6B:
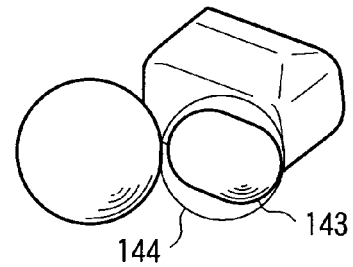

It is also possible to adjust the determined 3D-ROI in accordance with the instruction issued by the user via the input device 33. Subsequently, the apparatus changes the hues of voxels included in the 3D-ROI (step Sa9). The display unit 37 displays the VR image generated with the voxels whose hues have been changed (step Sa10). FIG. 6A is a view showing a case of changing the hues of a plurality of voxels 143 in a 3D-ROI 144 determined for the VR image displayed by the display unit 37. FIG. 6B is a view showing the VR image displayed in a line-of-sight direction different from that in FIG. 6A. FIGS. 6A and 6B indicate that even if the line-of-sight direction is changed, the 3D-ROI includes a region 143 as a diagnosis target.

According to the above arrangement, the following effects can be obtained.

According to this ultrasonic diagnosis apparatus, setting a 2D-ROI on one projected image including a target region will determine a 3D-ROI including the target region in the volume data. Therefore, the interpreting doctor or the like is only required to designate a 2D-ROI on one projected image including a target region or the like. This greatly reduces the operation load on the doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Second Embodiment)

The second embodiment will be described below with reference to the views of the accompanying drawing.

The difference from the first embodiment is that a 3D-ROI is determined based on the distance from the screen of a VR image along the line-of-sight direction at which the sum of voxel values included in a set three-dimensional region becomes maximum, instead of an average contribution value.

Figure 7:
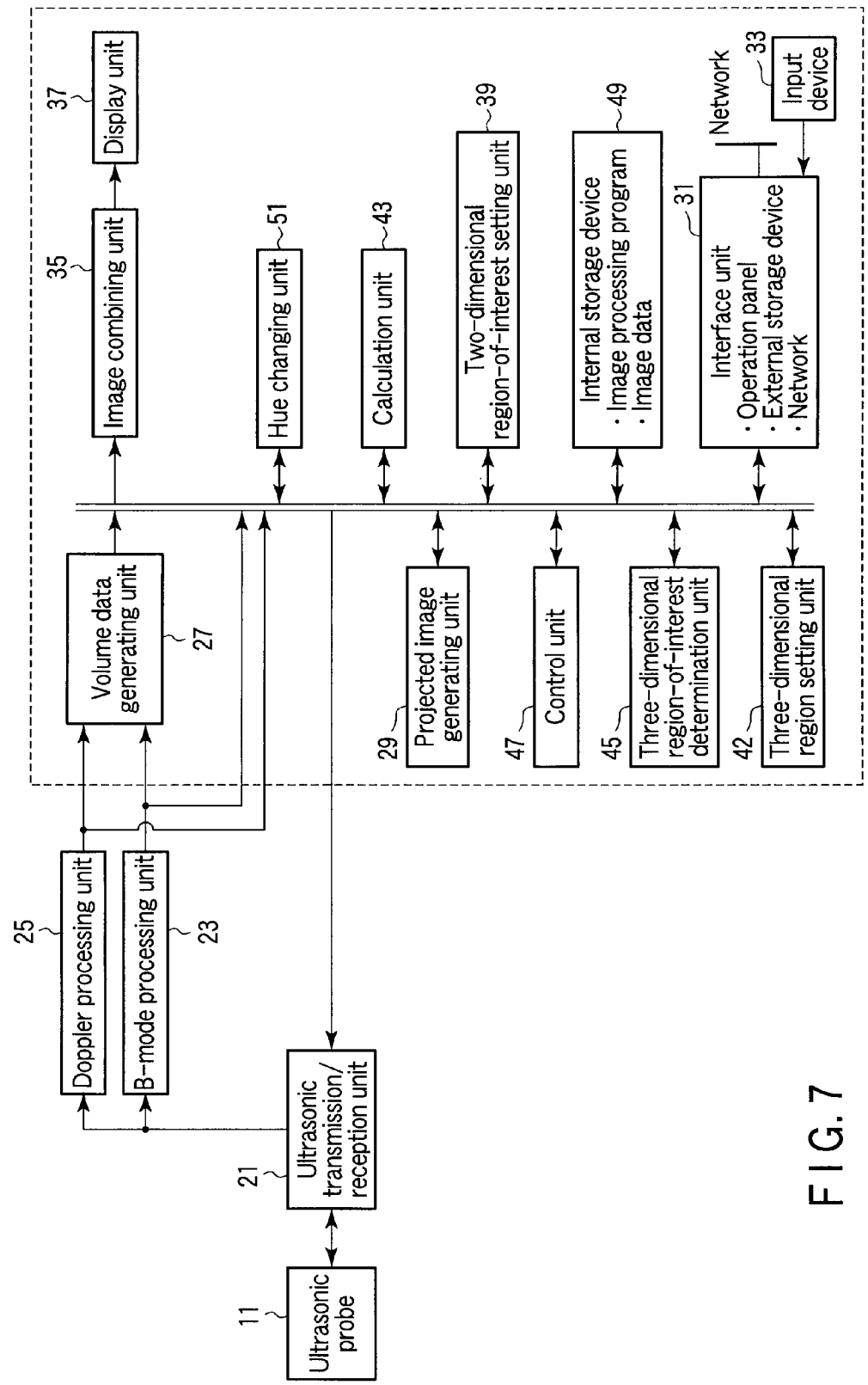
FIG. 7 is a block diagram showing the arrangement of an ultrasonic diagnosis apparatus according to the second embodiment.

FIG. 7 is a block diagram showing the arrangement of an ultrasonic diagnosis apparatus according to the second embodiment.

The constituent elements of the first and second embodiments which operate differently and a three-dimensional region setting unit 42 will be described below. Note that when the technical idea of this ultrasonic diagnosis apparatus is to be implemented by a medical image processing apparatus, the apparatus has, for example, the arrangement enclosed by the dotted line in FIG. 7.

The three-dimensional region setting unit 42 sets a three-dimensional region (to be referred to as a 3D-R (3-Dimensional Region) hereinafter), in volume data, which includes a 2D-ROI set on a VR image as a projection region in the line-of-sight direction set at the time of the generation of the VR image. In other words, a projection of the 3D-R in the line-of-sight direction includes a 2D-ROI. It is possible to set a 3D-R in an arbitrary shape. Note that it is possible to select the shape of a 3D-R from a template stored in an internal storage device 49 in advance in accordance with the instruction issued by the user via an input device 33. It is also possible to set the shape of a 3D-R in an arbitrary shape in accordance with the instruction issued by the user via the input device 33.

A calculation unit 43 calculates the sum of the voxel values included in a 3D-R (to be referred to as a 3DR voxel sum hereinafter). The calculation unit 43 moves the 3D-R along the line-of-sight direction. The calculation unit 43 calculates a 3DR voxel sum in the moved 3D-R. The calculation unit 43 repeats the movement and calculation until the 3D-R protrudes from the volume data. The internal storage device 49 stores the calculated 3DR voxel sum in correspondence with the distance from the screen of the VR image along the line-of-sight direction. A predetermined width is, for example, a constant number multiple of the length of a voxel along the line-of-sight direction. Note that this width can be changed in accordance with the instruction issued by the user via an input device.

The three-dimensional region-of-interest determination unit 45 specifies a 3DR voxel sum including the maximum value among the 3DR voxel sums stored in the internal storage device 49 for each predetermined width. The three-dimensional region-of-interest determination unit 45 determines the position of a 3D-ROI in the volume data based on the distance from the screen of the VR image at which the maximum value of the 3DR voxel sum is calculated.

The operation of a function of determining a 3D-ROI (to be referred to as a 3D-ROI determination function hereafter) in volume data in this ultrasonic diagnosis apparatus will be described next with reference to the flowchart shown in FIG. 8.

The processing in steps Sb5 to Sb9 which differs from that shown in FIG. 4 which is a flowchart associated with the first embodiment will be described below.

Figure 9A:
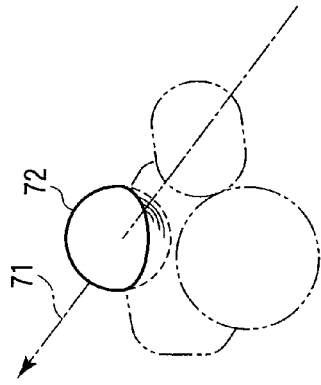
FIGS. 9A, 9B, and 9C are views each showing an example of a three-dimensional region moved a predetermined width at a time along the line-of-sight direction in the second embodiment.
Figure 9B:
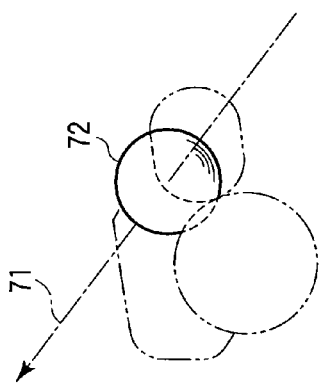
Figure 9C:
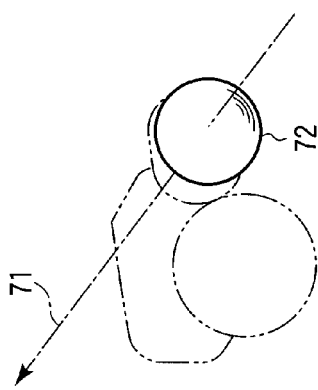

After step Sa4, the 3D-ROI determination function sets a 3D-R at a position nearest to the screen of the VR image in the volume data (step Sb5). Note that it is possible to set the 3D-R at a position farthest from the screen of the VR image in the volume data. Subsequently, this function calculates a 3DR voxel sum and stores it in the internal storage device 49 in correspondence with the distance from the screen of the VR image along the line-of-sight direction (step Sb6). The function then moves the 3D-R by a predetermined width in a direction to move away from (or move close to) the screen of the VR image along the line-of-sight direction (step Sb7). FIGS. 9A, 9B, and 9C show how a 3D-R 72 is moved a predetermined width at a time along a line-of-sight direction 71. That is, the 3D-R 72 moves to the positions shown in FIGS. 9A, 9B, and 9C in the alphabetical order.

The 3D-ROI determination function repeats the processing in steps Sb6 and Sb7 until the 3D-R protrudes from the volume data (step Sb8).

Figure 10:
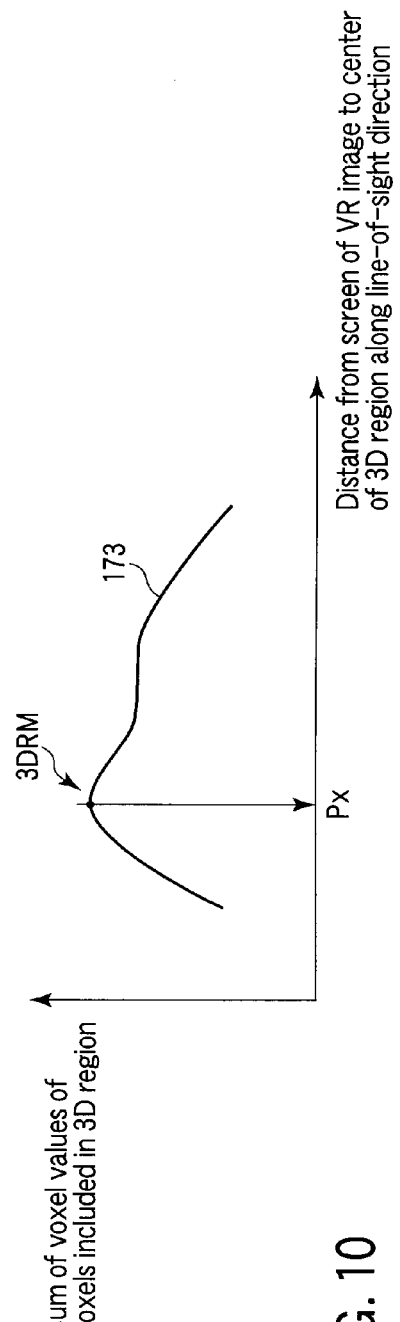
FIG. 10 is a graph of the sums of the voxel values included in a three-dimensional region which corresponds to the distances from the screen of a VR image to the center of the three-dimensional region along the line-of-sight direction according to the second embodiment.

The 3D-ROI determination function determines the position of the 3D-ROI in the volume data based on the distance from the screen of the VR image to the center of the 3D-R in which the maximum value of the 3DR voxel sum is calculated (step Sb9). FIG. 10 is a graph showing an example of the 3DR voxel sums corresponding to the distances from the screen of the VR image to the center of the three-dimensional region along the line-of-sight direction and the distance corresponding to the maximum value of the sums for the determination of a 3D-ROI. The graph in FIG. 10 shows a curve 173 obtained by plotting the 3DR voxel sums corresponding to the distances from the screen of the VR image along the line-of-sight direction. Reference symbol 3DRM denotes the maximum value of the 3D-R; and Px, the distance from the screen of the VR image along the line-of-sight direction which corresponds to 3DRM for the determination of a 3D-ROI. The three-dimensional region-of-interest determination unit 45 determines the position of the 3D-ROI in the volume data based on the distance Px. Assume that the determined position of the 3D-ROI is the center of gravity of the 3D-ROI. If, for example, the 3D-ROI is spherical, the position of the center of the 3D-ROI is determined in the volume data based on Px. Note that the three-dimensional region-of-interest determination unit 45 can also set by the user with regard to which part of the 3D-ROI is made to correspond to the position of the 3D-ROI determined based on Px via the input device 33.

According to the above arrangement, the following effects can be obtained.

According to this ultrasonic diagnosis apparatus, setting a 2D-ROI on one projected image including a target region will determine a 3D-ROI including the target region in the volume data. Therefore, the interpreting doctor or the like is only required to designate a 2D-ROI on one projected image including a target region. This greatly reduces the operation load on the doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Third Embodiment)

The third embodiment will be described below with reference to the views of the accompanying drawing.

The difference from the first and second embodiments is that a 3D-ROI is determined based on the distance from the screen of a VR image along the line-of-sight direction at which the sum of the voxel values included in a set three-dimensional region differs most from the sum of the voxel values included in a hull surrounding the three-dimensional region.

The block diagram of the third embodiment is the same as FIG. 7 which is the block diagram of the second embodiment. Those of the constituent elements of the first and second embodiments which operate differently and a three-dimensional region setting unit 42 will be described below. Note that when the technical idea of this ultrasonic diagnosis apparatus is to be implemented by a medical image processing apparatus, the apparatus has, for example, the arrangement enclosed by the dotted line in FIG. 7.

The three-dimensional region setting unit 42 sets a 3D-R and a hull surrounding the 3D-R (to be referred to as a 3D-H (3-Dimensional Hull) hereinafter) in volume data. It is possible to set a 3D-R and 3D-H in arbitrary shapes. Note that it is possible to select the shapes of a 3D-R and 3D-H from templates stored in an internal storage device 49 in advance in accordance with the instructions issued by the user via an input device 33. It is also possible to set the shapes of a 3D-R and 3D-H in arbitrary shapes in accordance with the instructions issued by the user via the input device 33.

A calculation unit 43 calculates the difference between the sum of voxel values included in 3D-R and the sum of the voxel values included in the 3D-H (to be referred to as the hull sum hereinafter). The calculation unit 43 operates the 3D-R and the 3D-H to move along the line-of-sight direction. The calculation unit 43 calculates the 3DR voxel sum in the moved 3D-R and the hull sum in the moved 3D-H. The calculation unit 43 repeats the movement and calculation until the 3D-H protrudes from the volume data. The internal storage device 49 stores the calculated differences in correspondence with the distances from the screen of the VR image along the line-of-sight direction.

A three-dimensional region-of-interest determination unit 45 specifies the maximum value of the difference from the differences stored in the internal storage device 49 for each predetermined width. The three-dimensional region-of-interest determination unit 45 determines the position of a 3D-ROI in the volume data based on the distance from the screen of the VR image at which the maximum value of the difference is calculated.

The operation of a function of determining a 3D-ROI (to be referred to as a 3D-ROI determination function hereinafter) in volume data in this ultrasonic diagnosis apparatus will be described next with reference to the flowchart shown in FIG. 11.

The processing in steps Sc5 to Sc9 which differs from that in FIG. 4 which is the flowchart associated with the first embodiment will be described below.

After step Sa4, the 3D-ROI determination function sets a 3D-R and a 3D-H as the hull surrounding the 3D-R at positions nearest to the screen of the VR image in the volume data (step Sc5). FIG. 12 shows an example of a 3D-R 181 and a 3D-H 182 surrounding the 3D-R. Note that it is possible to set the 3D-R and 3D-H at positions farthest from the screen of the VR image in the volume data. Subsequently, the 3D-ROI determination function calculates the difference between the sum of voxel values inside the 3D-R and that inside 3D-H. The internal storage device 49 stores the difference in correspondence with the distance from the screen of the VR image along the line-of-sight direction (step Sc6). This function then moves the 3D-R and the 3D-H by a predetermined width in a direction to move away from (or move close to) the screen of the VR image (step Sc7). The function repeats the process in steps Sc6 and Sc7 until the 3D-H protrudes from the volume data (step Sc8).

The 3D-ROI determination function determines the position of the 3D-ROI in the volume data based on the distance from the screen of the VR image to the center of the 3D-R at which the calculated difference between the sums of voxel values is the maximum (step Sc9). FIG. 13 is a graph showing the differences between the sum of voxel values inside the 3D-R and that inside the 3D-H corresponding to the distances from the screen of the VR image to the center of the 3D-R along the line-of-sight direction, as well as the distances corresponding to the maximum value of the difference for the determination of a 3D-ROI position. The graph in FIG. 13 shows a curve 183 obtained by plotting the 3DR voxel sums corresponding to the distances from the screen of the VR image along the line-of-sight direction. Reference symbol DM denotes the maximum value of the difference value; and Py, the distance from the screen of the VR image along the line-of-sight direction, which corresponds to DM. The three-dimensional region-of-interest determination unit 45 determines the position of the 3D-ROI in the volume data based on Py.

According to the above arrangement, the following effects can be obtained.

This ultrasonic diagnosis apparatus can determine a 3D-ROI including a target region when regions larger than the 3D-ROI including large voxel values exist in front or back of the 3D-ROI in the line-of-sight direction. In addition, setting a 2D-ROI on one projected image including a target region will determine a 3D-ROI including the target region in the volume data. Therefore, the interpreting doctor or the like is only required to designate a 2D-ROI on one projected image including a target region. This greatly reduces the operation load on the doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Fourth Embodiment)

The fourth embodiment will be described below with reference to the views of the accompanying drawing.

The difference from the first to third embodiments is that a 3D-ROI is determined based on two different line-of-sight directions.

Figure 14:
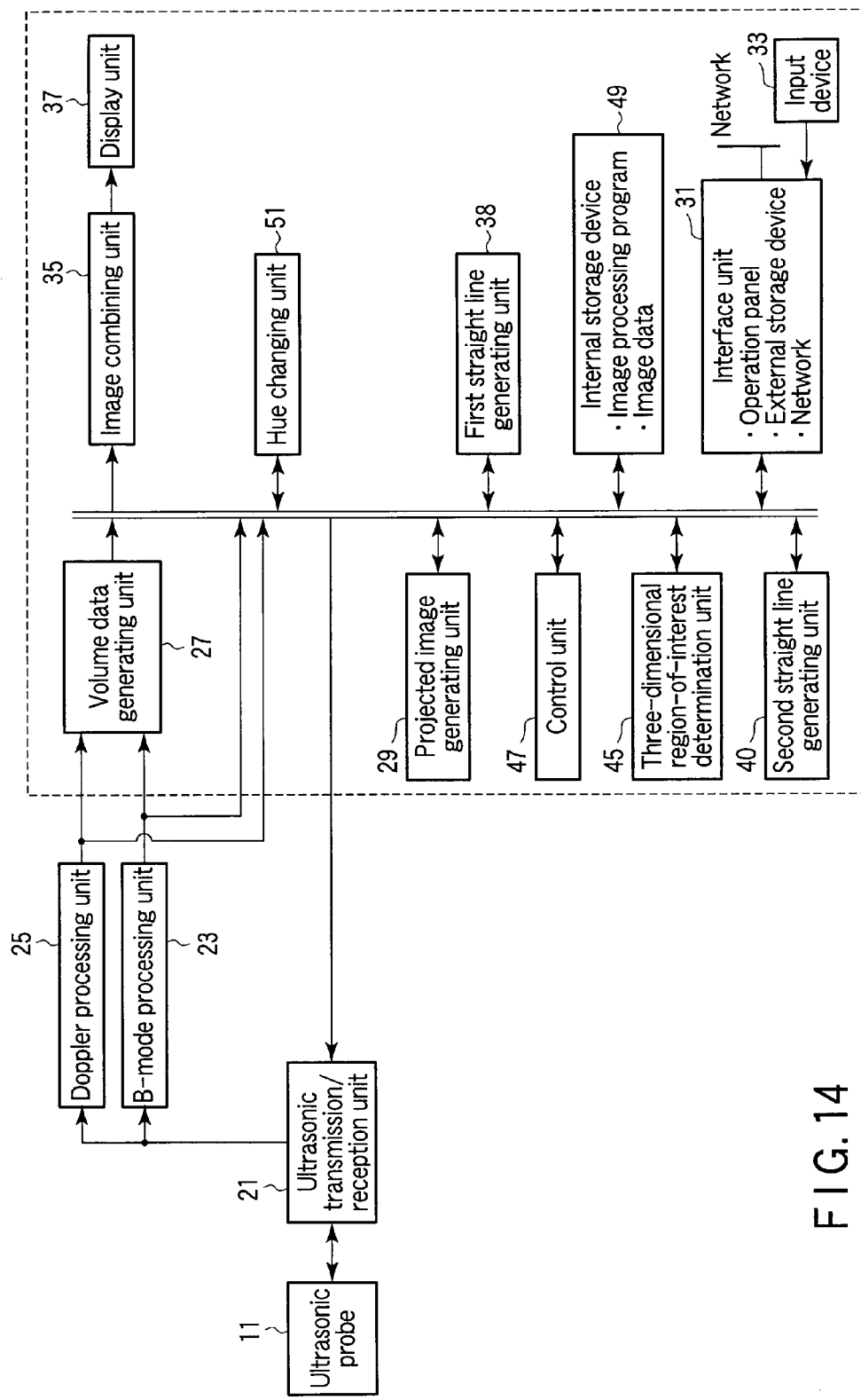
FIG. 14 is a block diagram showing the arrangement of an ultrasonic diagnosis apparatus according to the fourth embodiment.

FIG. 14 is a block diagram showing the arrangement of an ultrasonic diagnosis apparatus according to the fourth embodiment.

The constituent elements of the first to third embodiments which operate differently, a first straight line generating unit 38, and a second straight line generating unit 40 will be described below. Note that when the technical idea of this ultrasonic diagnosis apparatus is to be implemented by a medical image processing apparatus, the apparatus has, for example, the arrangement enclosed by the dotted line in FIG. 14.

The first straight line generating unit 38 sets the first point on the first VR image generated by a projected image generating unit 29 in accordance with the instruction issued by the user via an input device 33, and generates the first straight line with the first point and the first line-of-sight direction used to generate the first VR image. An internal storage device 49 stores the position information of the first straight line in the volume data.

The second straight line generating unit 40 sets the second point on the second VR image generated by the projected image generating unit 29 in accordance with the instruction issued by the user via an input device 33, and generates the second straight line with the second point and the second line-of-sight direction used to generate the second VR image. The internal storage device 49 stores the position information of the second straight line in the volume data.

A three-dimensional region-of-interest determination unit 45 generates the first and second straight lines on volume data. When these straight lines have a relationship of a skew position, the three-dimensional region-of-interest determination unit 45 determines a predetermined internally dividing point with respect to the shortest distance between these straight lines as the position of a 3D-ROI. The skew position is a state of non-crossing and non-parallelism associated with the first and the second straight line in a three-dimensional space. The predetermined internally dividing point is, for example, the midpoint of the shortest distance. When these straight lines intersect each other, the three-dimensional region-of-interest determination unit 45 determines the intersection of these straight lines as the position of the 3D-ROI.

The operation of a function of determining a 3D-ROI (to be referred to as a 3D-ROI determination function hereinafter) in volume data in this ultrasonic diagnosis apparatus will be described next with reference to the flowchart shown in FIG. 15.

The processing in steps Sd4 to Sd10 which differs from that in FIG. 4 which is a flowchart associated with the first embodiment will be described below.

The projected image generating unit 29 generates the first VR image based on volume data and the first line-of-sight direction set by the user via the input device 33. The 3D-ROI determination function sets the first point on the first VR image in accordance with the instruction issued by the user via the input device 33 (step Sd4). This function generates the first straight line with the first line-of-sight direction and the first point (step Sd5). FIG. 16A shows a first straight line 1stl generated by a first straight line generating unit 38, together with a first VR image 1stVR and a first point 1stP.

The projected image generating unit 29 generates the second VR image based on volume data and the second line-of-sight direction set by the user via the input device 33. The 3D-ROI determination function sets the second point on the second VR image in accordance with the instruction issued by the user via the input device 33 (step Sd6). This function generates the second straight line with the second line-of-sight direction and the second point (step Sd7). FIG. 16B shows a second straight line 2ndl generated by the second straight line generating unit 40, together with a second VR image 2ndVR and a second point 2ndP.

The three-dimensional region-of-interest determination unit 45 determines whether the first and second straight lines have the relationship of the skew position (step Sd8). If the first and second straight lines have the relationship of the skew position, the three-dimensional region-of-interest determination unit 45 determines a predetermined internally dividing point with respect to the shortest distance between the first and second straight lines as the position of a 3D-ROI (step Sd9). If the first and second straight lines do not have the relationship of the skew position, i.e., the first and second straight lines intersect each other, the three-dimensional region-of-interest determination unit 45 determines the intersection of the first and second straight lines as the position of a 3D-ROI (step Sd10). FIG. 16C shows that a 3D-ROI is determined when the first and second straight lines have the relationship of the skew position. Referring to FIG. 16C, reference symbol L denotes the shortest distance between the first straight line 1stl and the second straight line 2ndl; and 3DP, the midpoint of L which is the center of the 3D-ROI. FIG. 16C shows a 3D-ROI in a spherical shape as an example.

According to the above arrangement, the following effects can be obtained.

According to this ultrasonic diagnosis apparatus, setting one point in each of target regions on two projected images based on different line-of-sight directions will determine a 3D-ROI including the target region in the volume data. Therefore, the interpreting doctor or the like is only required to designate one point on the two projected images each including a target region. This greatly reduces the operation load on the doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Fifth Embodiment)

The fifth embodiment will be described below with reference to the views of the accompanying drawing.

A medical image diagnosis apparatus according to the fifth embodiment has the arrangement enclosed by the dotted line in FIG. 1. When, for example, the medical image diagnosis apparatus is an X-ray computed tomography (to be referred to as a CT hereinafter) apparatus, the X-ray CT apparatus has the arrangement enclosed by the dotted line. Note that the medical image diagnosis apparatus may be an X-ray diagnosis apparatus, nuclear magnetic resonance apparatus, positron emission computed tomography apparatus, or single photon emission computed tomography apparatus. In addition, the medical image diagnosis apparatus of this embodiment may be any type of apparatus as long as it is a medical image diagnosis apparatus which generates volume data.

The operation of a function of determining a 3D-ROI (to be referred to as a 3D-ROI determination function hereinafter) in volume data in this medical image diagnosis apparatus will be described next with reference to the flowchart shown in FIG. 17.

A volume data generating unit 27 generates volume data (step Se1). The 3D-ROI determination function generates a VR image based on the generated volume data and the input predetermined line-of-sight direction (step Se2). This function sets a 2D-ROI on the VR image in accordance with the instruction issued by the user via an input device 33 (step Se3). The process in steps Se4 to Se9 corresponds to the process in steps Sa5 to Sa10 in FIG. 4.

According to the above arrangement, the following effects can be obtained.

According to this medical image diagnosis apparatus, setting a 2D-ROI on one projected image including a target region will determine a 3D-ROI including the target region in the volume data. Therefore, the interpreting doctor or the like is only required to designate a 2D-ROI on one projected image including a target region. This greatly reduces the operation load on the interpreting doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Sixth Embodiment)

The sixth embodiment will be described below with reference to the views of the accompanying drawing.

A medical image diagnosis apparatus according to the sixth embodiment has the arrangement enclosed by the dotted line in FIG. 7. When, for example, the medical image diagnosis apparatus is an X-ray CT apparatus, the X-ray CT apparatus has the arrangement enclosed by the dotted line. Note that the medical image diagnosis apparatus may be an X-ray diagnosis apparatus, nuclear magnetic resonance apparatus, positron emission computed tomography apparatus, or single photon emission computed tomography apparatus. In addition, the medical image diagnosis apparatus of this embodiment may be any type of apparatus as long as it is a medical image diagnosis apparatus which generates volume data.

The operation of a function of determining a 3D-ROI (to be referred to as a 3D-ROI determination function hereinafter) in volume data in this medical image diagnosis apparatus will be described next with reference to the flowchart shown in FIG. 18.

After step Se3, the processing in steps Sf4 to Sf8 corresponds to the processing in steps Sb5 to Sb9 in FIG. 8.

According to the above arrangement, the following effects can be obtained.

According to this medical image diagnosis apparatus, setting a 2D-ROI on one projected image including a target region will determine a 3D-ROI including the target region in the volume data. Therefore, the interpreting doctor or the like is only required to designate a 2D-ROI on one projected image including a target region. This greatly reduces the operation load on the interpreting doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Seventh Embodiment)

The seventh embodiment will be described below with reference to the views of the accompanying drawing.

A medical image diagnosis apparatus according to the seventh embodiment has the arrangement enclosed by the dotted line in FIG. 7. When, for example, the medical image diagnosis apparatus is an X-ray CT apparatus, the X-ray CT apparatus has the arrangement enclosed by the dotted line. Note that the medical image diagnosis apparatus may be an X-ray diagnosis apparatus, nuclear magnetic resonance apparatus, positron emission computed tomography apparatus, or single photon emission computed tomography apparatus. In addition, the medical image diagnosis apparatus of this embodiment may be any type of apparatus as long as it is a medical image diagnosis apparatus which generates volume data.

The operation of a function of determining a 3D-ROI (to be referred to as a 3D-ROI determination function hereinafter) in volume data in this medical image diagnosis apparatus will be described next with reference to the flowchart shown in FIG. 19.

Figure 11:
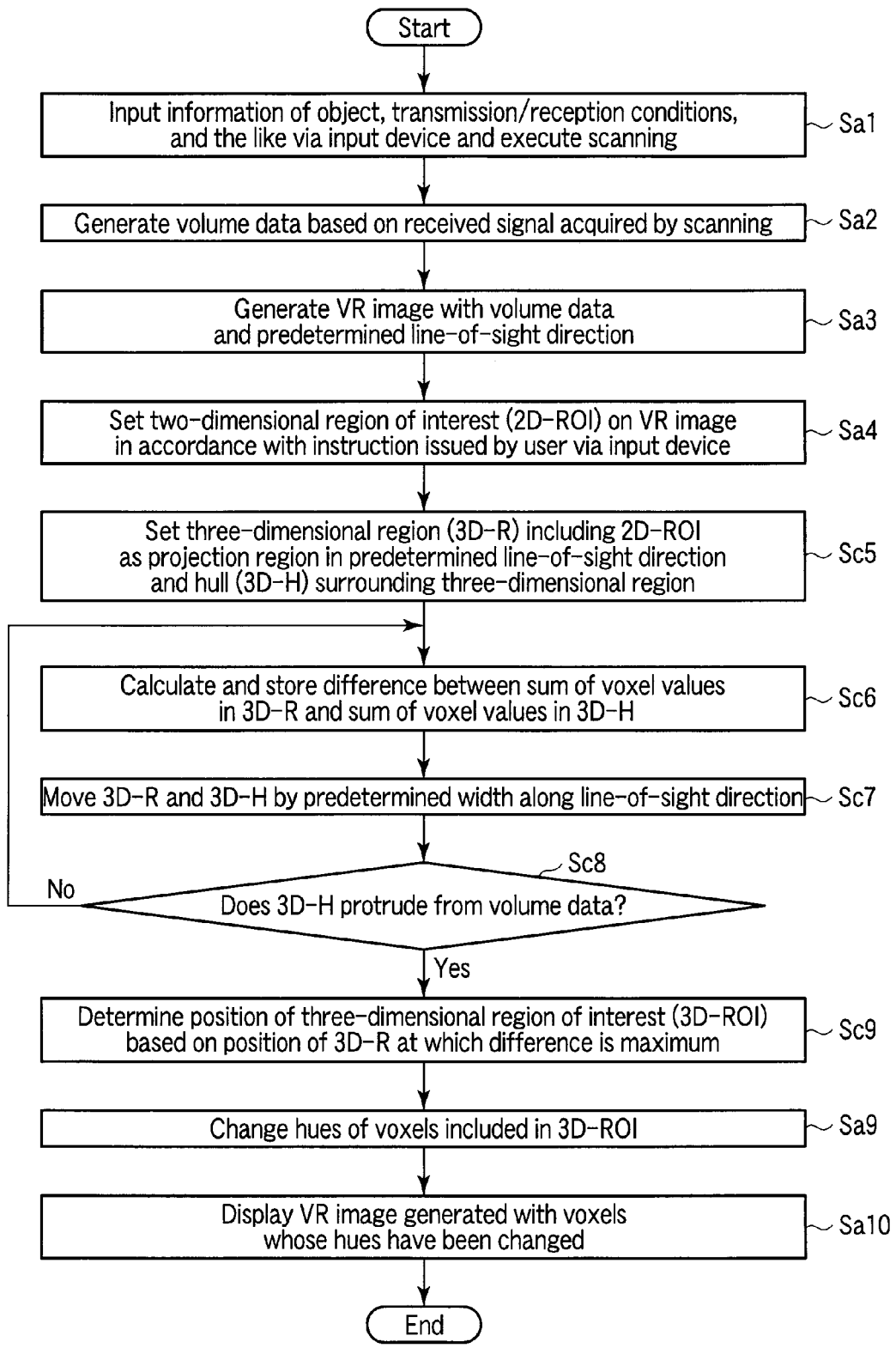
FIG. 11 is a flowchart showing a procedure for determining a 3D-ROI based on a three-dimensional region including a 2D-ROI as its projection with a predetermined line-of-sight direction and the hull surrounding the three-dimensional region in the third embodiment.

After step Se3, the processing in steps Sf4 to Sf8 corresponds to the processing in steps Sc5 to Sc9 in FIG. 11.

According to the above arrangement, the following effects can be obtained.

This medical image diagnosis apparatus can determine a 3D-ROI including a target region when regions larger than the 3D-ROI including large voxel values exist in front or back of the 3D-ROI in the line-of-sight direction corresponding to a projected image. In addition, setting a 2D-ROI on one projected image including a target region will determine a 3D-ROI including the target region in the volume data. Therefore, the interpreting doctor or the like is only required to designate a 2D-ROI on one projected image including a target region. This greatly reduces the operation load on the interpreting doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

(Eighth Embodiment)

The eighth embodiment will be described below with reference to the views of the accompanying drawing.

A medical image diagnosis apparatus according to the eighth embodiment has the arrangement enclosed by the dotted line in FIG. 14. When, for example, the medical image diagnosis apparatus is an X-ray CT apparatus, the X-ray CT apparatus has the arrangement enclosed by the dotted line. Note that the medical image diagnosis apparatus may be an X-ray diagnosis apparatus, nuclear magnetic resonance apparatus, positron emission computed tomography apparatus, or single photon emission computed tomography apparatus. In addition, the medical image diagnosis apparatus of this embodiment may be any type of apparatus as long as it is a medical image diagnosis apparatus which generates volume data.

The operation of a function of determining a 3D-ROI (to be referred to as a 3D-ROI determination function hereinafter) in volume data in this medical image diagnosis apparatus will be described next with reference to the flowchart shown in FIG. 20.

Figure 15:
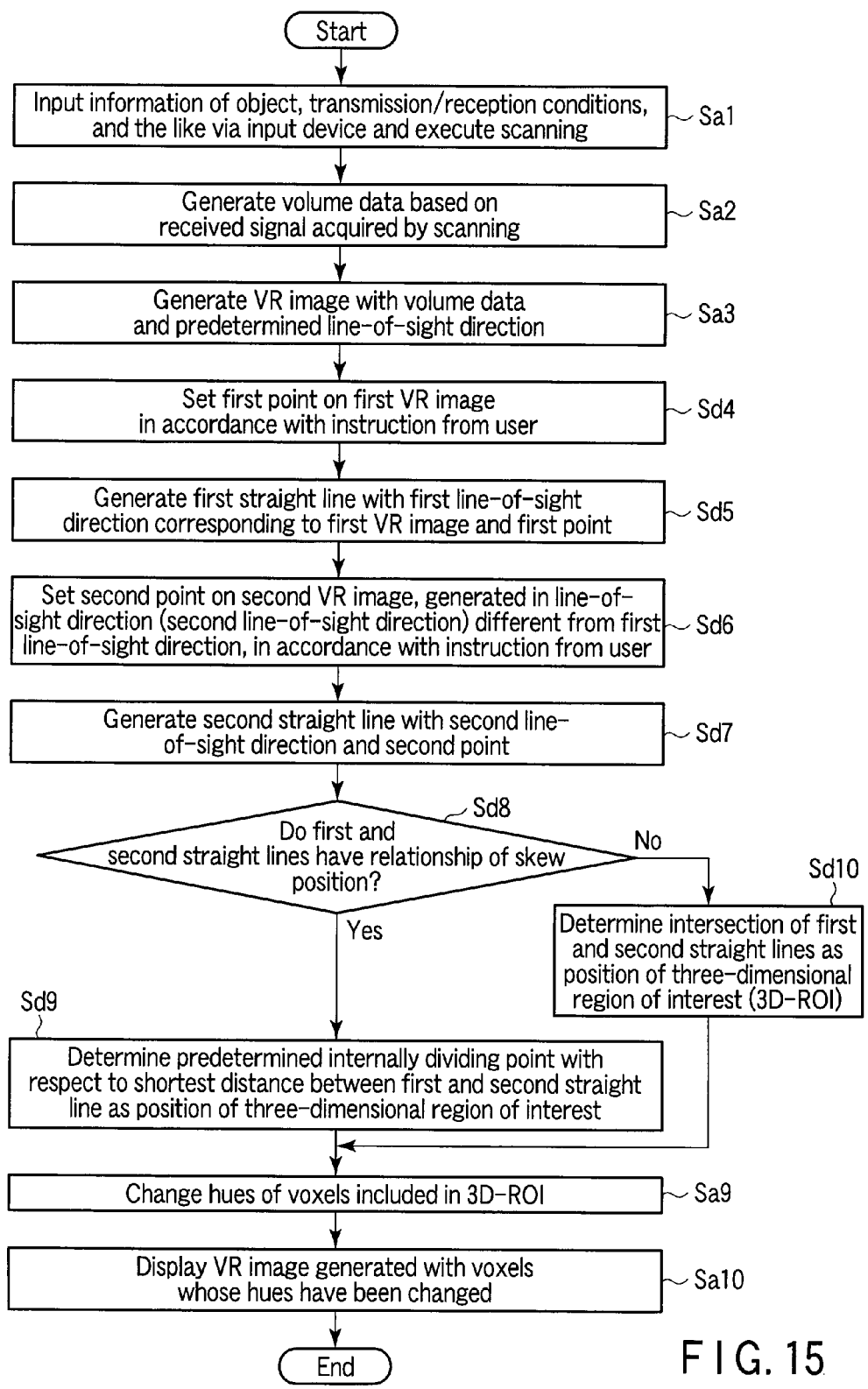
FIG. 15 is a flowchart showing a procedure for determining a 3D-ROI based on two line-of-sight directions which are not parallel in the fourth embodiment.

After step Se2, the processing in steps Sh3 to Sh9 corresponds to the processing in steps Sd4 to Sd10 in FIG. 15.

According to the above arrangement, the following effects can be obtained.

According to this medical image diagnosis apparatus, setting one point in each of target regions on two projected images based on different line-of-sight directions will determine a 3D-ROI including the target region in the volume data. Therefore, the interpreting doctor or the like is only required to designate one point on the two projected images each including a target region. This greatly reduces the operation load on the interpreting doctor or the like. In addition, since the interpreting doctor or the like performs the above operation on a displayed image, he/she need not grasp the sequential correspondence between three-dimensional images and two-dimensional images. This prevents the interpreting doctor or the like from being confused. As described above, this apparatus can improve the operability and operation efficiency for the interpreting doctor or the like and allows him/her to easily and quickly determine a 3D-ROI.

Each function associated with each embodiment can also be implemented by installing programs for executing the corresponding processing in a computer such as a workstation and expanding them in a memory. In this case, the programs which can operate the computer to execute the corresponding techniques can be distributed by being stored in recording media such as magnetic disks (floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus comprising:
an ultrasonic probe;
an ultrasonic transmission/reception unit configured to transmit an ultrasonic wave to an object and receive a reflected wave corresponding to the transmitted ultrasonic wave from the object via the ultrasonic probe and to generate a received signal based on the received reflected wave;
a volume data generating unit configured to generate volume data based on the received signal;
a projected image generating unit configured to generate a projected image based on the volume data and a predetermined line-of-sight direction;
a two-dimensional region-of-interest setting unit configured to set a two-dimensional region of interest on the projected image;
a specifying unit configured to specify a plurality of voxels based on pixels in the two-dimensional region of interest and the predetermined line-of-sight direction;
a calculation unit configured to calculate a contribution degree of each of the specified voxels which contributes to a value of the pixels in the two-dimensional region of interest based on a voxel value and opacity of each of the plurality of voxels; and
a three-dimensional region-of-interest determination unit configured to determine a position of a three-dimensional region of interest in the volume data based on the contribution degree.

2. The apparatus according to claim 1, further comprising:
a hue changing unit configured to change hues of voxels included in the three-dimensional region of interest; and
a display unit configured to display at least one of a projected image and a slice image generated based on the voxels whose hues are changed.

3. An ultrasonic diagnosis apparatus comprising:
an ultrasonic probe;
an ultrasonic transmission/reception unit configured to transmit an ultrasonic wave to an object and receive a reflected wave corresponding to the transmitted ultrasonic wave from the object via the ultrasonic probe and to generate a received signal based on the received reflected wave;
a volume data generating unit configured to generate volume data based on the received signal;
a projected image generating unit configured to generate a projected image based on the volume data and a predetermined line-of-sight direction;
a two-dimensional region-of-interest setting unit configured to set a two-dimensional region of interest on the projected image;
a three-dimensional region setting unit configured to set a three-dimensional region including the two-dimensional region of interest as a projection with the predetermined line-of-sight direction;
a calculation unit configured to calculate a sum of voxel values included in a set three-dimensional region moved by a predetermined width along the predetermined line-of-sight direction every time the set three-dimensional region is moved by the predetermined width; and
a three-dimensional region-of-interest determination unit configured to determine, as a position of a three-dimensional region of interest, a position of the three-dimensional region, in the volume data, in which a sum of the voxel values is a maximum value.

4. An ultrasonic diagnosis apparatus comprising:
an ultrasonic probe;
an ultrasonic transmission/reception unit configured to transmit an ultrasonic wave to an object and receive a reflected wave corresponding to the transmitted ultrasonic wave from the object via the ultrasonic probe and to generate a received signal based on the received reflected wave;
a volume data generating unit configured to generate volume data based on the received signal;
a projected image generating unit configured to generate a projected image based on the volume data and a predetermined line-of-sight direction;
a two-dimensional region-of-interest setting unit configured to set a two-dimensional region of interest on the projected image;
a three-dimensional region setting unit configured to set a three-dimensional region including the two-dimensional region of interest as a projection with the predetermined line-of-sight direction and a hull surrounding the three-dimensional region;
a calculation unit configured to calculate a difference between a sum of voxel values included in a three-dimensional region moved by a predetermined width along the predetermined line-of-sight direction and a sum of voxel values included in the hull, every time the three-dimensional region is moved by the predetermined width; and
a three-dimensional region-of-interest determination unit configured to determine, as a position of a three-dimensional region of interest, a position of the three-dimensional region, in the volume data, at which the difference becomes maximum.

5. An ultrasonic diagnosis apparatus comprising:
an ultrasonic probe;
an ultrasonic transmission/reception unit configured to transmit an ultrasonic wave to an object and receive a reflected wave corresponding to the transmitted ultrasonic wave from the object via the ultrasonic probe and to generate a received signal based on the received reflected wave;
a volume data generating unit configured to generate volume data based on the received signal;
a projected image generating unit configured to generate a projected image based on the volume data and a predetermined line-of-sight direction;
a first straight line generating unit configured to generate a first straight line by setting a first point on a first projected image generated by the projected image generating unit and using the first point and a first line-of-sight direction corresponding to the first projected image;
a second straight line generating unit configured to generate a second straight line by setting a second point on a second projected image generated by the projected image generating unit and using the second point and a second line-of-sight direction corresponding to the second projected image; and
a three-dimensional region-of-interest determination unit configured to determine a predetermined internally dividing point with respect to a shortest distance between the first straight line and the second straight line as a position of a three-dimensional region of interest when the first straight line and the second straight line include a relationship of a skew position and to determine an intersection of the first straight line and the second straight line as a position of a three-dimensional region of interest when the first straight line and the second straight line intersect each other.

6. A medical image processing apparatus comprising:
a volume data generating unit configured to generate volume data associated with a predetermined region of an object;
a projected image generating unit configured to generate a projected image based on the volume data and a predetermined line-of-sight direction;
a two-dimensional region-of-interest setting unit configured to set a two-dimensional region of interest on the projected image;
a specifying unit configured to specify a plurality of voxels based on pixels in the two-dimensional region of interest and the predetermined line-of-sight direction;
a calculation unit configured to calculate a contribution degree of each of the specified voxels which contributes to a value of the pixels in the two-dimensional region of interest based on a voxel value and opacity of each of the plurality of voxels; and
a three-dimensional region-of-interest determination unit configured to determine a position of a three-dimensional region of interest in the volume data based on the contribution.

7. The apparatus according to claim 6, further comprising:
a hue changing unit configured to change hues of voxels included in the three-dimensional region of interest; and
a display unit configured to display at least one of a projected image and a slice image generated based on the voxels whose hues are changed.

8. A medical image processing apparatus comprising:
a volume data generating unit configured to generate volume data associated with a predetermined region of an object;
a projected image generating unit configured to generate a projected image based on the volume data and a predetermined line-of-sight direction;
a two-dimensional region-of-interest setting unit configured to set a two-dimensional region of interest on the projected image;
a three-dimensional region setting unit configured to set a three-dimensional region including the two-dimensional region of interest as a projection with the predetermined line-of-sight direction;
a calculation unit configured to calculate a sum of voxel values included in a three-dimensional region moved by a predetermined width along the predetermined line-of-sight direction every time the set three-dimensional region is moved by the predetermined width; and
a three-dimensional region-of-interest determination unit configured to determine, as a position of a three-dimensional region of interest, a position of the three-dimensional region, in the volume data, in which a sum of the voxel values is a maximum value.

9. A medical image processing apparatus comprising:
a volume data generating unit configured to generate volume data associated with a predetermined region of an object;
a projected image generating unit configured to generate a projected image based on the volume data and a predetermined line-of-sight direction;
a two-dimensional region-of-interest setting unit configured to set a two-dimensional region of interest on the projected image;
a three-dimensional region setting unit configured to set a three-dimensional region including the two-dimensional region of interest as a projection with the predetermined line-of-sight direction and a hull surrounding the three-dimensional region;

a calculation unit configured to calculate a difference between a sum of voxel values included in the a three-dimensional region moved by a predetermined width along the predetermined line-of-sight direction and a sum of voxel values included in the hull, every time the three-dimensional region is moved by the predetermined width; and a three-dimensional region-of-interest determination unit configured to determine, as a position of a three-dimensional region of interest, a position of the three-dimensional region, in the volume data, at which the difference becomes maximum.

10. A medical image processing apparatus comprising:

a volume data generating unit configured to generate volume data associated with a predetermined region of an object;

a projected image generating unit configured to generate a projected image based on the volume data and a predetermined line-of-sight direction;

a first straight line generating unit configured to generate a first straight line by setting a first point on a first projected image generated by the projected image generating unit and using the first point and a first line-of-sight direction corresponding to the first projected image;

a second straight line generating unit configured to generate a second straight line by setting a second point on a second projected image generated by the projected image generating unit and using the second point and a second line-of-sight direction corresponding to the second projected image; and a three-dimensional region-of-interest determination unit configured to determine a predetermined internally dividing point with respect to a shortest distance between the first straight line and the second straight line as a position of a three-dimensional region of interest when the first straight line and the second straight line include a relationship of a skew position and to determine an intersection of the first straight line and the second straight line as a position of a three-dimensional region of interest when the first straight line and the second straight line intersect each other.

11. A medical image diagnosis apparatus comprising:

a volume data generating unit configured to generate volume data associated with a predetermined region of an object;

a projected image generating unit configured to generate a projected image based on the volume data and a predetermined line-of-sight direction;

a two-dimensional region-of-interest setting unit configured to set a two-dimensional region of interest on the projected image;

a specifying unit configured to specify a plurality of voxels based on pixels in the two-dimensional region of interest and the predetermined line-of-sight direction;

a calculation unit configured to calculate a contribution degree of each of the specified voxels which contributes to a value of the pixels in the two-dimensional region of interest based on a voxel value and opacity of each of the plurality of voxels; and a three-dimensional region-of-interest determination unit configured to determine a position of a three-dimensional region of interest in the volume data based on the contribution.

12. The apparatus according to claim 11, further comprising:

a hue changing unit configured to change hues of voxels included in the three-dimensional region of interest; and a display unit configured to display at least one of a projected image and a slice image generated based on the voxels whose hues are changed.

13. A medical image diagnosis apparatus comprising:

a volume data generating unit configured to generate volume data associated with a predetermined region of an object;

a projected image generating unit configured to generate a projected image based on the volume data and a predetermined line-of-sight direction;

a two-dimensional region-of-interest setting unit configured to set a two-dimensional region of interest on the projected image;

a three-dimensional region setting unit configured to set a three-dimensional region including the two-dimensional region of interest as a projection with the predetermined line-of-sight direction;

a calculation unit configured to calculate a sum of voxel values included in the three-dimensional region; and a three-dimensional region-of-interest determination unit configured to determine a position of a three-dimensional region of interest in the volume data based on the sum of the voxel values.

14. A medical image diagnosis apparatus comprising:

a volume data generating unit configured to generate volume data associated with a predetermined region of an object;

a projected image generating unit configured to generate a projected image based on the volume data and a predetermined line-of-sight direction;

a two-dimensional region-of-interest setting unit configured to set a two-dimensional region of interest on the projected image;

a three-dimensional region setting unit configured to set a three-dimensional region including the two-dimensional region of interest as a projection with predetermined line-of-sight direction and a hull surrounding the three-dimensional region;

a calculation unit configured to calculate a difference between a sum of voxel values included in the three-dimensional region and a sum of voxel values included in the hull; and a three-dimensional region-of-interest determination unit configured to determine a position of a three-dimensional region of interest in the volume data based on the difference.

15. A medical image diagnosis apparatus comprising:

a volume data generating unit configured to generate volume data associated with a predetermined region of an object;

a projected image generating unit configured to generate a projected image based on the volume data and a predetermined line-of-sight direction;

a first straight line generating unit configured to generate a first straight line by setting a first point on a first projected image generated by the projected image generating unit and using the first point and a first line-of-sight direction corresponding to the first projected image;

a second straight line generating unit configured to generate a second straight line by setting a second point on a second projected image generated by the projected image generating unit and using the second point and a second line-of-sight direction corresponding to the second projected image; and a three-dimensional region-of-interest determination unit configured to determine a predetermined internally dividing point with respect to a shortest distance between the first straight line and the second straight line as a position of a three-dimensional region of interest when the first straight line and the second straight line include a relationship of a skew position and to determine an intersection of the first straight line and the second straight line as a position of a three-dimensional region of interest when the first straight line and the second straight line intersect each other.

16. A medical image processing apparatus comprising:

a storage unit configured to store volume data associated with an object;

a projected image generating unit configured to generate a projected image comprising a plurality of projection pixels respectively corresponding to a plurality of projection lines from the volume data; and a calculation unit configured to calculate a contribution degree of each of a plurality of voxels on a specific projection line corresponding to at least one specific projection pixel of the projection pixels, the contribution degree is a degree in which a voxel value of each of the voxels contributes to a pixel value of the specific projection pixel, based on at least one of an accumulated value of voxel values associated with a voxel located on one of two sides of each of the voxels on the specific projection line and an accumulated value of voxel values associated with a voxel located on the other of the two sides.

* * * * *